(12) United States Patent
Bellin et al.

(10) Patent No.: US 9,128,031 B2
(45) Date of Patent: Sep. 8, 2015

(54) METHOD TO IMPROVE THE LEACHING PROCESS

(75) Inventors: Federico Bellin, The Woodlands, TX (US); Vamsee Chintamaneni, Houston, TX (US)

(73) Assignee: VAREL INTERNATIONAL IND., L.P., Carrollton, TX (US)

( * ) Notice: Subject to any disclaimer, the term of this patent is extended or adjusted under 35 U.S.C. 154(b) by 656 days.

(21) Appl. No.: 13/428,635

(22) Filed: Mar. 23, 2012

(65) Prior Publication Data
US 2013/0247478 A1 Sep. 26, 2013

Related U.S. Application Data

(63) Continuation-in-part of application No. 13/401,452, filed on Feb. 21, 2012.

(51) Int. Cl.
| | | |
|---|---|---|
| *B24D 3/00* | (2006.01) | |
| *B24D 3/02* | (2006.01) | |
| *B24D 11/00* | (2006.01) | |
| *B24D 18/00* | (2006.01) | |
| *C09K 3/14* | (2006.01) | |
| *C09C 1/68* | (2006.01) | |
| *G01N 27/22* | (2006.01) | |

(Continued)

(52) U.S. Cl.
CPC ............... *G01N 27/221* (2013.01); *B22F 3/24* (2013.01); *E21B 10/00* (2013.01); *B22F 7/06* (2013.01); *B22F 2003/244* (2013.01); *C22C 26/00* (2013.01); *E21B 10/56* (2013.01)

(58) Field of Classification Search
USPC ........................................... 51/307, 293, 308
See application file for complete search history.

(56) References Cited

U.S. PATENT DOCUMENTS

| | | | |
|---|---|---|---|
| 2,755,240 A | | 7/1956 | Normore et al. |
| 2,934,811 A | * | 5/1960 | Wellington .................. 29/25.42 |

(Continued)

FOREIGN PATENT DOCUMENTS

| | | |
|---|---|---|
| DE | 102005040296 | 2/2007 |
| WO | 2013003333 | 1/2013 |

OTHER PUBLICATIONS

Copenheaver, Blaine R, International Search Report and Written Opinion of the International Searching Authority for PCT/US2013/026938, Apr. 25, 2013, pp. 1-13.

(Continued)

*Primary Examiner* — James McDonough
(74) *Attorney, Agent, or Firm* — King & Spalding LLP

(57) ABSTRACT

A method to leach a component that includes a polycrystalline structure. The method includes obtaining the component having the polycrystalline structure. The polycrystalline structure includes catalyst material deposited therein. The method also includes performing a leaching process on the polycrystalline structure to an intermediate leaching depth. The leaching process removes at least a portion of the catalyst material from the polycrystalline structure and forms one or more by-product materials deposited therein. The method also includes performing a cleaning process on the polycrystalline structure, which removes at least a portion of the by-product materials. The leaching process and the cleaning process are iteratively continued until the intermediate leaching depth reaches a desired leaching depth, both of which are measured from one end of the polycrystalline structure. The desired leaching depth is greater than at least one intermediate leaching depth.

18 Claims, 10 Drawing Sheets

(51) Int. Cl.
*E21B 10/00* (2006.01)
*B22F 3/24* (2006.01)
*C22C 26/00* (2006.01)
*B22F 7/06* (2006.01)
*E21B 10/56* (2006.01)

(56) References Cited

U.S. PATENT DOCUMENTS

| | | | |
|---|---|---|---|
| 4,255,976 A * | 3/1981 | Formato | 73/861.08 |
| 4,290,016 A * | 9/1981 | Lorenzi | 324/216 |
| 4,952,869 A | 8/1990 | Tuttle | |
| 6,063,333 A | 5/2000 | Dennis | |
| 6,107,808 A | 8/2000 | McKee et al. | |
| 6,388,453 B1 | 5/2002 | Greer | |
| 6,437,579 B1 | 8/2002 | Yamashita et al. | |
| 7,558,369 B1 | 7/2009 | Mourik et al. | |
| 7,616,734 B1 * | 11/2009 | Corbett et al. | 378/46 |
| 7,712,553 B2 | 5/2010 | Shamburger | |
| 7,757,792 B2 | 7/2010 | Shamburger | |
| 8,014,492 B1 | 9/2011 | Corbett et al. | |
| 8,080,074 B2 | 12/2011 | Sani | |
| 2002/0053904 A1 | 5/2002 | Chen et al. | |
| 2002/0179864 A1 | 12/2002 | Fielden | |
| 2005/0050801 A1 | 3/2005 | Cho et al. | |
| 2006/0244443 A1 | 11/2006 | Goldfine et al. | |
| 2007/0079994 A1 | 4/2007 | Middlemiss | |
| 2007/0131458 A1 | 6/2007 | Shen et al. | |
| 2007/0169419 A1 | 7/2007 | Davis et al. | |
| 2008/0054891 A1 | 3/2008 | Dobsky | |
| 2008/0104034 A1 | 5/2008 | Stewart et al. | |
| 2008/0121433 A1 | 5/2008 | Ledgerwood | |
| 2008/0164887 A1 | 7/2008 | Schroder | |
| 2008/0223623 A1 | 9/2008 | Keshavan et al. | |
| 2008/0241024 A1 | 10/2008 | Riekkola-Vanhanen et al. | |
| 2008/0290866 A1 | 11/2008 | Cuffe et al. | |
| 2009/0152018 A1 | 6/2009 | Sani | |
| 2009/0173015 A1 | 7/2009 | Keshavan et al. | |
| 2010/0011673 A1 | 1/2010 | Shamburger | |
| 2010/0095602 A1 * | 4/2010 | Belnap et al. | 51/309 |
| 2010/0155149 A1 | 6/2010 | Keshavan et al. | |
| 2010/0231208 A1 | 9/2010 | Huggett et al. | |
| 2011/0120782 A1 | 5/2011 | Cooley et al. | |
| 2011/0215814 A1 | 9/2011 | Dorrough | |
| 2011/0258936 A1 | 10/2011 | DiGiovanni | |
| 2012/0047815 A1 | 3/2012 | Sani | |
| 2012/0055717 A1 | 3/2012 | Liversage et al. | |
| 2012/0067652 A1 | 3/2012 | Bellin | |
| 2012/0211284 A1 | 8/2012 | DiGiovanni | |
| 2012/0241224 A1 | 9/2012 | Qian et al. | |
| 2013/0213433 A1 | 8/2013 | Bellin et al. | |
| 2013/0213720 A1 | 8/2013 | Bellin et al. | |
| 2013/0214768 A1 | 8/2013 | Chintamaneni et al. | |
| 2013/0214769 A1 | 8/2013 | King et al. | |
| 2013/0214799 A1 | 8/2013 | Bellin et al. | |
| 2013/0248258 A1 | 9/2013 | Bellin et al. | |
| 2014/0062509 A1 | 3/2014 | Bellin et al. | |

OTHER PUBLICATIONS

Copenheaver, Blaine R, International Search Report and Written Opinion of the International Searching Authority for PCT/US2013/026918, Apr. 23, 2013, pp. 1-11.

Copenheaver, Blaine R, International Search Report and Written Opinion of the International Searching Authority for PCT/US2013/026931, Apr. 26, 2013, pp. 1-10.

Bellin et al., "The Current State of PDC Bit Technology Part 2 of 3: Leaching a Thin Layer at the Working Surface of a PDC Cutter to Remove the Cobalt Dramatically Reduces Diamond Degradation Due to Frictional Heat", Oct. 1, 2010, pp. 1-18, Retrieved from the Internet: URL: http://www.varelintl.com/content/includes/world_oil_october 2010.pdf [retrieved on Mar. 18, 2014].

Bellin et al., "The Current State of PDC Bit Technology Part 2 of 3: Improvements in Material Properties and Testing Methods Are Being Pursued to Make PDC The Cutter of Choice for an Increasing Variety of Applications" Nov. 1, 2010, pp. 67-71, Retrieved from the Internet: URL: http://www.varelintl.com/content/includes/pdc_technology_part_3.pdf.

Pierson, Hugh O., Chapter 12: Natural High-Pressure Synthetic Diamond, Handbook of Carbon, Graphite, Diamond and Fullerences, Properties, Processing and Applications, Jan. 1, 1993, pp. 278-301, Noyes Publications.

Kraus, Leonie, European Search Report EP Application No. 13156142, Mar. 19, 2014, 7 pages, place of search The Hague.

Kraus, Leonie, European Search Report EP Application No. 13156143, Feb. 19, 2014, 6 pages, place of search The Hague.

Grove et al., Determining Dielectric Constants Using a Parallel Plate Capacitor, American Journal of Physics 73 (1), Jan. 2005, entire document. [retrieved on Apr. 4, 2013]. Retrieved form Internet <URL: http://users.df.uba.ar/sgil/physics_paper_doc/papers_phys/e&m/dielectr_const_2k4.pdf>entire document.

Translation of Description of WO/2007022749 corresponding to International Application No. PCT/DE2006/001376 "Measuring Method for In-Situ Control of the Chemical Etching Process of Latent Ion Tracks in a Dielectric Substrate" printed on Nov. 14, 2004, 4 pages, http://patentscope.wipo.int/search/en/detail/jsf, unofficial translation via Google translate.

Gill Jennings & Avery LLP, Henry Hunt-Grubbe, Response to extended European Search Report (EESR) issued in European Patent Application No. 13156142.5, dated Oct. 30, 2014, 25 pages.

Thomas, Shane, International Search Report and Written Opinion issued in PCT/US2014/064359, completed on Jan. 18, 2015, 11 pages, United States Patent and Trademark Office, Alexandria, Virginia, United States.

Forestier, Gilles, European Search Report issued in European Patent Application No. 13156140.9,completed on Jan. 12, 2015, 8 pages, European Patent Office, The Hague.

Forestier, Gilles, European Search Report issued in European Patent Application No. 13156138.3, completed on Jan. 12, 2015, 8 pages, European Patent Office, The Hague.

\* cited by examiner

METHOD TO IMPROVE THE LEACHING PROCESS

RELATED APPLICATIONS

The present application is a continuation-in-part of U.S. patent application Ser. No. 13/401,452, entitled "Method to Improve the Performance of a Leached Cutter" and filed on Feb. 21, 2012, which is incorporated by reference herein.

The present application is related to U.S. patent application Ser. No. 13/401,188, entitled "Use of Capacitance to Analyze Polycrystalline Diamond" and filed on Feb. 21, 2012, and U.S. patent application Ser. No. 13/401,335, entitled "Use of Capacitance and Eddy Currents to Analyze Polycrystalline Diamond" and filed on Feb. 21, 2012, which are all incorporated by reference herein.

TECHNICAL FIELD

The present invention is directed generally to methods of leaching components having a polycrystalline structure. More particularly, the present invention is directed to methods of leaching components having a polycrystalline structure that include one or more cycles of a leaching process and a cleaning process, where the leaching process removes at least a portion of the catalyst materials present within the polycrystalline structure and the cleaning process removes at least a portion of the by-product materials formed during the leaching process and present within the polycrystalline structure.

BACKGROUND

Polycrystalline diamond compacts ("PDC") have been used in industrial applications, including rock drilling applications and metal machining applications. Such compacts have demonstrated advantages over some other types of cutting elements, such as better wear resistance and impact resistance. The PDC can be formed by sintering individual diamond particles together under the high pressure and high temperature ("HPHT") conditions referred to as the "diamond stable region," which is typically above forty kilobars and between 1,200 degrees Celsius and 2,000 degrees Celsius, in the presence of a catalyst/solvent which promotes diamond-diamond bonding. Some examples of catalyst/solvents for sintered diamond compacts are cobalt, nickel, iron, and other Group VIII metals. PDCs usually have a diamond content greater than seventy percent by volume, with about eighty percent to about ninety-eight percent being typical. An unbacked PDC can be mechanically bonded to a tool (not shown), according to one example. Alternatively, the PDC is bonded to a substrate, thereby forming a PDC cutter, which is typically insertable within, or mounted to, a downhole tool (not shown), such as a drill bit or a reamer.

FIG. 1 shows a side view of a PDC cutter 100 having a polycrystalline diamond ("PCD") cutting table 110, or compact, in accordance with the prior art. Although a PCD cutting table 110 is described in the exemplary embodiment, other types of cutting tables, including polycrystalline boron nitride ("PCBN") compacts, are used in alternative types of cutters. Referring to FIG. 1, the PDC cutter 100 typically includes the PCD cutting table 110 and a substrate 150 that is coupled to the PCD cutting table 110. The PCD cutting table 110 is about one hundred thousandths of an inch (2.5 millimeters) thick; however, the thickness is variable depending upon the application in which the PCD cutting table 110 is to be used.

The substrate 150 includes a top surface 152, a bottom surface 154, and a substrate outer wall 156 that extends from the circumference of the top surface 152 to the circumference of the bottom surface 154. The PCD cutting table 110 includes a cutting surface 112, an opposing surface 114, and a PCD cutting table outer wall 116 that extends from the circumference of the cutting surface 112 to the circumference of the opposing surface 114. The opposing surface 114 of the PCD cutting table 110 is coupled to the top surface 152 of the substrate 150. Typically, the PCD cutting table 110 is coupled to the substrate 150 using a high pressure and high temperature ("HPHT") press. However, other methods known to people having ordinary skill in the art can be used to couple the PCD cutting table 110 to the substrate 150. In one embodiment, upon coupling the PCD cutting table 110 to the substrate 150, the cutting surface 112 of the PCD cutting table 110 is substantially parallel to the substrate's bottom surface 154. Additionally, the PDC cutter 100 has been illustrated as having a right circular cylindrical shape; however, the PDC cutter 100 is shaped into other geometric or non-geometric shapes in other exemplary embodiments. In certain exemplary embodiments, the opposing surface 114 and the top surface 152 are substantially planar; however, the opposing surface 114 and the top surface 152 is non-planar in other exemplary embodiments. Additionally, according to some exemplary embodiments, a bevel (not shown) is formed around at least a portion of the circumference of the cutting surface 112.

According to one example, the PDC cutter 100 is formed by independently forming the PCD cutting table 110 and the substrate 150, and thereafter bonding the PCD cutting table 110 to the substrate 150. Alternatively, the substrate 150 is initially formed and the PCD cutting table 110 is subsequently formed on the top surface 152 of the substrate 150 by placing polycrystalline diamond powder onto the top surface 152 and subjecting the polycrystalline diamond powder and the substrate 150 to a high temperature and high pressure process. Alternatively, the substrate 150 and the PCD cutting table 110 are formed and bonded together at about the same time. Although a few methods of forming the PDC cutter 100 have been briefly mentioned, other methods known to people having ordinary skill in the art can be used.

According to one example for forming the PDC cutter 100, the PCD cutting table 110 is formed and bonded to the substrate 150 by subjecting a layer of diamond powder and a mixture of tungsten carbide and cobalt powders to HPHT conditions. The cobalt is typically mixed with tungsten carbide and positioned where the substrate 150 is to be formed. The diamond powder is placed on top of the cobalt and tungsten carbide mixture and positioned where the PCD cutting table 110 is to be formed. The entire powder mixture is then subjected to HPHT conditions so that the cobalt melts and facilitates the cementing, or binding, of the tungsten carbide to form the substrate 150. The melted cobalt also diffuses, or infiltrates, into the diamond powder and acts as a catalyst for synthesizing diamond bonds and forming the PCD cutting table 110. Thus, the cobalt acts as both a binder for cementing the tungsten carbide and as a catalyst/solvent for sintering the diamond powder to form diamond-diamond bonds. The cobalt also facilitates in forming strong bonds between the PCD cutting table 110 and the cemented tungsten carbide substrate 150.

Cobalt has been a preferred constituent of the PDC manufacturing process. Traditional PDC manufacturing processes use cobalt as the binder material for forming the substrate 150 and also as the catalyst material for diamond synthesis because of the large body of knowledge related to using cobalt in these processes. The synergy between the large bodies of knowledge and the needs of the process have led to using cobalt as both the binder material and the catalyst material. However, as is known in the art, alternative metals, such as iron, nickel, chromium, manganese, and tantalum, and other suitable materials, can be used as a catalyst for diamond synthesis. When using these alternative materials as a catalyst for diamond synthesis to form the PCD cutting table 110, cobalt, or some other material such as nickel chrome or iron, is typically used as the binder material for cementing the tungsten carbide to form the substrate 150. Although some materials, such as tungsten carbide and cobalt, have been provided as examples, other materials known to people having ordinary skill in the art can be used to form the substrate 150, the PCD cutting table 110, and form bonds between the substrate 150 and the PCD cutting table 110.

FIG. 2 is a schematic microstructural view of the PCD cutting table 110 of FIG. 1 in accordance with the prior art. Referring to FIGS. 1 and 2, the PCD cutting table 110 has diamond particles 210 bonded to other diamond particles 210, one or more interstitial spaces 212 formed between the diamond particles 210, and cobalt 214 deposited within the interstitial spaces 212. During the sintering process, the interstitial spaces 212, or voids, are formed between the carbon-carbon bonds and are located between the diamond particles 210. The diffusion of cobalt 214 into the diamond powder results in cobalt 214 being deposited within these interstitial spaces 212 that are formed within the PCD cutting table 110 during the sintering process.

Once the PCD cutting table 110 is formed and placed into operation, the PCD cutting table 110 is known to wear quickly when the temperature reaches a critical temperature. This critical temperature is about 750 degrees Celsius and is reached when the PCD cutting table 110 is cutting rock formations or other known materials. The high rate of wear is believed to be caused by the differences in the thermal expansion rate between the diamond particles 210 and the cobalt 214 and also by the chemical reaction, or graphitization, that occurs between cobalt 214 and the diamond particles 210. The coefficient of thermal expansion for the diamond particles 210 is about $1.0 \times 10^{-6}$ millimeters$^{-1} \times$Kelvin$^{-1}$ ("mm$^{-1}$K$^{-1}$"), while the coefficient of thermal expansion for the cobalt 214 is about $13.0 \times 10^{-6}$ mm$^{-1}$K$^{-1}$. Thus, the cobalt 214 expands much faster than the diamond particles 210 at temperatures above this critical temperature, thereby making the bonds between the diamond particles 210 unstable. The PCD cutting table 110 becomes thermally degraded at temperatures above about 750 degrees Celsius and its cutting efficiency deteriorates significantly.

Efforts have been made to slow the wear of the PCD cutting table 110 at these high temperatures. These efforts include performing conventional acid leaching processes of the PCD cutting table 110 which removes some of the cobalt 214, or catalyst material, from the interstitial spaces 212. Conventional leaching processes involve the presence of an acid solution (not shown) which reacts with the cobalt 214, or other binder/catalyst material, that is deposited within the interstitial spaces 212 of the PCD cutting table 110. These acid solutions typically consist of highly concentrated solutions of hydrofluoric acid (HF), nitric acid ($HNO_3$), and/or sulfuric acid ($H_2SO_4$) and are subjected to different temperature and pressure conditions. According to one example of a conventional leaching process, the PDC cutter 100 is placed within an acid solution such that at least a portion of the PCD cutting table 110 is submerged within the acid solution. The acid solution reacts with the cobalt 214, or other binder/catalyst material, along the outer surfaces of the PCD cutting table 110. The acid solution slowly moves inwardly within the interior of the PCD cutting table 110 and continues to react with the cobalt 214. During the reaction, one or more by-product materials 398 (FIG. 3) are formed. These by-product materials 398 (FIG. 3) are usually water soluble and dissolve within the solution; however, these by-product materials 398 (FIG. 3) become trapped in the interstitial spaces 21 when the concentration becomes too high and they precipitate out of solution. As more by-product material 398 (FIG. 3) become trapped within the PCD cutting table 110, the acid solution moves inwardly at even a slower rate; and hence, the rate of leaching slows down considerably within these conventional leaching processes. For this reason, a tradeoff occurs between conventional leaching process duration and the desired leaching depth, wherein costs increase as the conventional leaching process duration increases. Thus, the leaching depth is typically about 0.2 millimeters, which takes about days to achieve this depth. However, the leached depth can be more or less depending upon the PCD cutting table 110 requirements and/or the cost constraints. The removal of cobalt 214 alleviates the issues created due to the differences in the thermal expansion rate between the diamond particles 210 and the cobalt 214 and due to graphitization. Although it has been described that conventional leaching processes are used to remove at least some of the catalyst 214, other leaching processes or catalyst removal processes can be used to remove at least some of the catalyst 214 from the interstitial spaces 212.

FIG. 3 shows a cross-section view of a leached PDC cutter 300 having a PCD cutting table 310 that has been at least partially leached in accordance with the prior art. Referring to FIG. 3, the PDC cutter 300 includes the PCD cutting table 310 coupled to a substrate 350. The substrate 350 is similar to substrate 150 (FIG. 1) and is not described again for the sake of brevity. The substrate 350 includes a top surface 365, a bottom surface 364, and a substrate outer wall 366 extending from the perimeter of the top surface 365 to the perimeter of the bottom surface 364. The PCD cutting table 310 is similar to the PCD cutting table 110 (FIG. 1), but includes a leached layer 354 and an unleached layer 356. The leached layer 354 extends from the cutting surface 312, which is similar to the cutting surface 112 (FIG. 1), towards an opposing surface 314, which is similar to the opposing surface 114 (FIG. 1). In the leached layer 354, at least a portion of the cobalt 214 has been removed from within the interstitial spaces 212 (FIG. 2) using at least one leaching process mentioned above. Thus, the leached layer 354 has been leached to a desired depth 353. However, as previously mentioned above, one or more by-product materials 398 are formed and deposited within some of the interstitial spaces 212 (FIG. 2) in the leached layer 354 during the leaching process. These by-product materials 398 are chemical by-products, or catalyst salts, of the dissolution reaction which are trapped within the open porosity of the interstitial spaces 212 (FIG. 2) during and/or after the dissolution process has been completed. The unleached layer 356 is similar to the PCD cutting table 150 (FIG. 1) and extends from the end of the leached layer 354 to the opposing surface 314. In the unleached layer 356, the cobalt 214 (FIG. 2) remains within the interstitial spaces 212 (FIG. 2) and has not been removed. Although a boundary line 355 is formed between the leached layer 354 and the unleached layer 356 and is depicted as being substantially linear, the boundary line 355 can be non-linear.

The leached PDC cutters 300 are leached to different desired depths 353 and how deep the cutter 300 has been leached has an effect on the performance of the cutter 300. As previously mentioned, the conventional leaching process is very slow, and thus, leached PDC cutters 300 that have been leached using the conventional leaching process become more expensive as the leaching depth increases. The cost of producing the leached PDC cutters 300 can be decreased if the rate of leaching were to increase. Further, the presence of by-product materials 398 within the leached layer 354 negatively impacts the performance of the leached PDC cutter 300.

BRIEF DESCRIPTION OF THE DRAWINGS

The foregoing and other features and aspects of the invention are best understood with reference to the following description of certain exemplary embodiments, when read in conjunction with the accompanying drawings, wherein.

Figure 1:
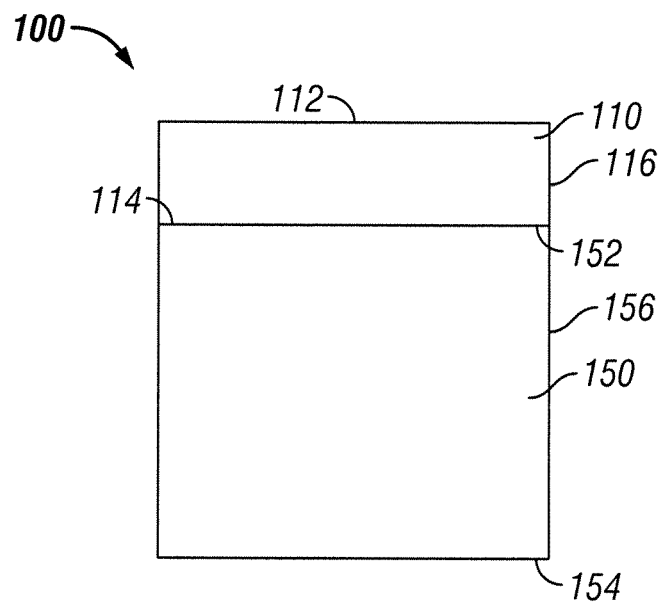
FIG. 1 shows a side view of a PDC cutter having a PCD cutting table in accordance with the prior art.

The drawings illustrate only exemplary embodiments of the invention and are therefore not to be considered limiting of its scope, as the invention may admit to other equally effective embodiments.

BRIEF DESCRIPTION OF EXEMPLARY EMBODIMENTS

The present invention is directed generally to methods of leaching components having a polycrystalline structure. More particularly, the present invention is directed to methods of leaching components having a polycrystalline structure that include one or more cycles of a leaching process and a cleaning process, where the leaching process removes at least a portion of the catalyst materials present within the polycrystalline structure and the cleaning process removes at least a portion of the by-product materials formed during the leaching process and also present within the polycrystalline structure. Each additional leaching process and cleaning process removes catalyst materials and by-product materials, respectively, from deeper within the polycrystalline structure. The cleaning process allows the next leaching process to perform at a faster rate than if the cleaning process did not happen. Although the description of exemplary embodiments is provided below in conjunction with a polycrystalline diamond compact ("PDC") cutter, alternate embodiments of the invention may be applicable to other types of cutters or components including, but not limited to, polycrystalline boron nitride ("PCBN") cutters or PCBN compacts. As previously mentioned, the compact is mountable to a substrate to form a cutter or is mountable directly to a tool for performing cutting processes. The invention is better understood by reading the following description of non-limiting, exemplary embodiments with reference to the attached drawings, wherein like parts of each of the figures are identified by like reference characters, and which are briefly described as follows.

Figure 4:
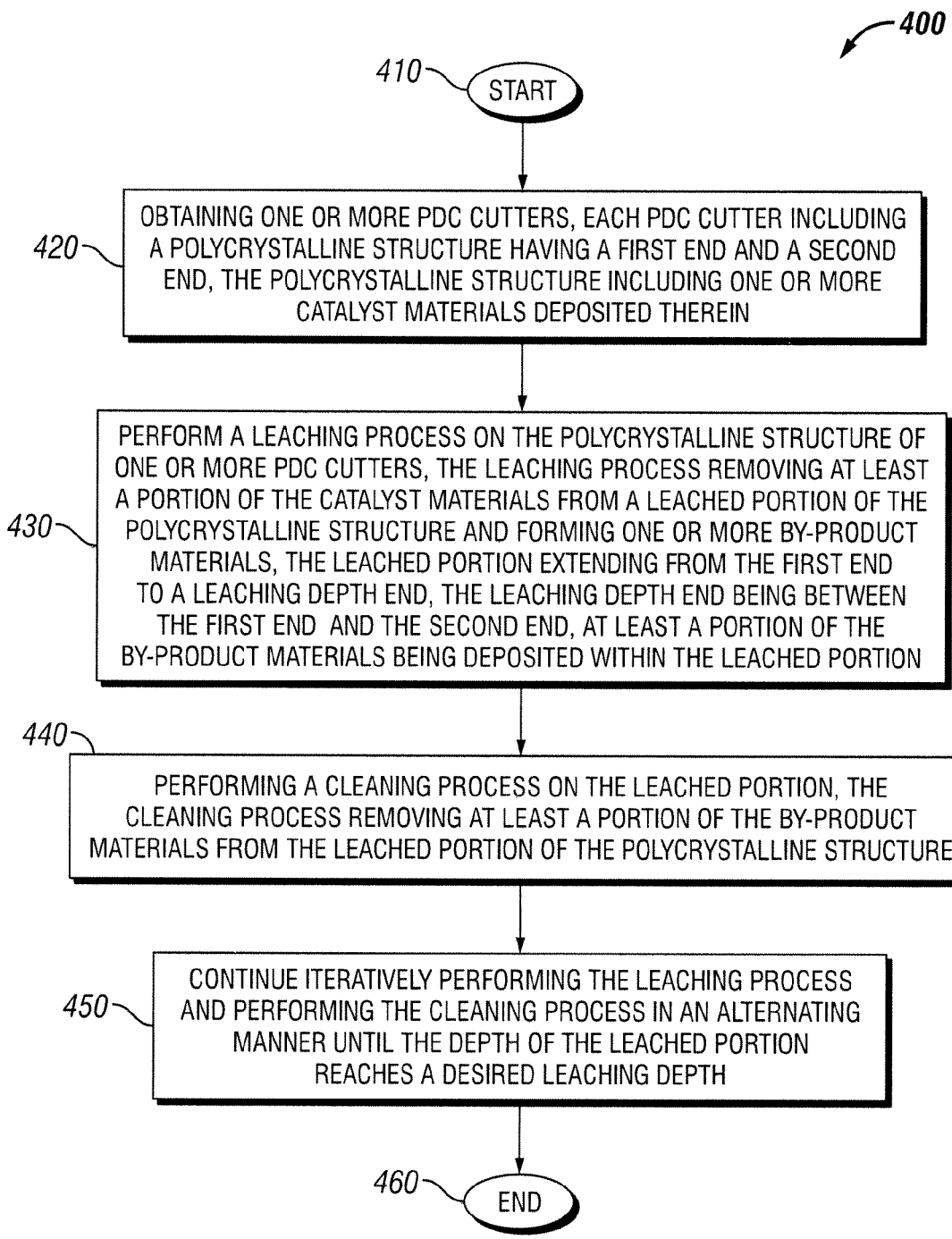
FIG. 4 is a flowchart depicting a leaching method in accordance with an exemplary embodiment of the present invention.

FIG. 4 is a flowchart depicting a leaching method 400 in accordance with an exemplary embodiment of the present invention. Although FIG. 4 shows a series of steps depicted in a certain order, the order of one or more steps can be rearranged, combined into fewer steps, and/or separated into more steps than that shown in other exemplary embodiments. Referring to FIG. 4, the leaching method 400 begins at step 410. Upon starting at step 410, the leaching method 400 proceeds to step 420. At step 420, one or more PDC cutters are obtained. According to certain exemplary embodiments, each PDC cutter includes a polycrystalline structure having a first end and a second end. The polycrystalline structure also includes one or more catalyst materials deposited therein. These PDC cutters have been described above in detail with respect to FIGS. 1 and 2 and therefore are not described again for the sake of brevity.

The leaching method 400 proceeds to step 430. At step 430, a leaching process is performed on the polycrystalline structure of one or more PDC cutters. The leaching process removes at least a portion of the catalyst materials from a leached portion of the polycrystalline structure and forms one or more by-product materials. The leached portion extends from the first end to a leaching depth end, where the leaching depth end is between the first end and the second end. At least a portion of the by-product materials is deposited within the leached portion. The leaching process continues until the rate of leaching decreases below a desired leaching threshold, which is determined by a user. Alternatively, the leaching process continues for a desired leaching period, which also is determined by the user. The desired leaching period ranges from a few minutes to several hours or days, if desired. PLEASE PROVIDE RATE RANGES AND TIME PERIODS IF AVAILABLE. Hence, at step 430, an intermediately leached PDC cutter 500 (FIG. 5) is formed.

Figure 3:
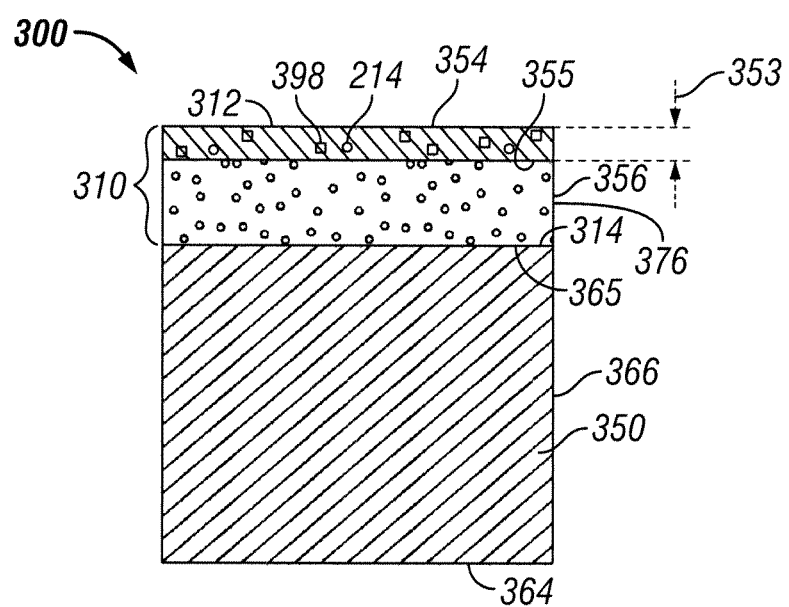
FIG. 3 shows a cross-sectional view of a leached PDC cutter having a PCD cutting table that has been at least partially leached in accordance with the prior art.
Figure 5:
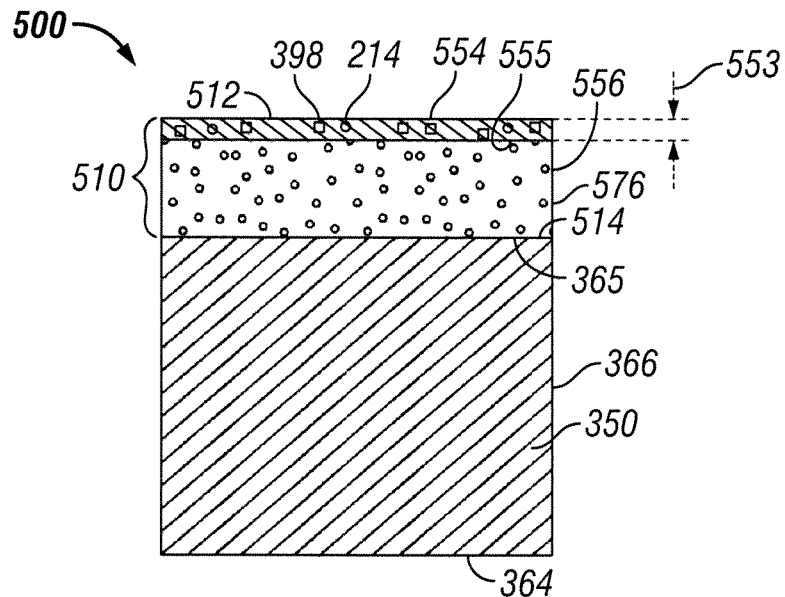
FIG. 5 shows a cross-sectional view of an intermediately leached PDC cutter in accordance with an exemplary embodiment of the present invention.

FIG. 5 shows a cross-sectional view of the intermediately leached PDC cutter 500 in accordance with an exemplary embodiment of the present invention. Referring to FIG. 5, the intermediately leached PDC cutter 500 includes the PCD cutting table 510, which is a polycrystalline structure, coupled to the substrate 350. The substrate 350 has been previously described with respect to FIG. 3 and is not described again for the sake of brevity. The PCD cutting table 510 is similar to the PCD cutting table 310 (FIG. 3), but includes a leached layer 554 and an unleached layer 556 having different depths, or thicknesses, than the leached layer 354 (FIG. 3) and the unleached layer 356 (FIG. 3), respectively, of the leached PDC cutter 300 (FIG. 3). The leached layer 554 also is referred to herein as a leached portion 554. Specifically, the leached portion 554 has a smaller depth, or smaller thickness, than leached layer 354 (FIG. 3). Also, the unleached layer 556 has a greater depth, or greater thickness, than the unleached layer 356 (FIG. 3). Hence, the depth of the leached portion 554, or an intermediate leaching depth 553 according to some exemplary embodiments, within the intermediately leached PDC cutter 500 has not yet reached the leaching depth 353 (FIG. 3), or desired leaching depth, of the leached PDC cutter 300 (FIG. 3). The intermediately leached PDC cutter 500 is formed using a leaching process for a shorter time period than when forming the leached PDC cutter 300 (FIG. 3).

The leached portion 554 extends from the cutting surface 512, or first end, which is similar to the cutting surface 312 (FIG. 3), towards an opposing surface 514, or second end, which is similar to the opposing surface 314 (FIG. 3). In the leached portion 554, at least a portion of the cobalt 214 has been removed from within the interstitial spaces 212 (FIG. 2) using at least one leaching process, which is described in further detail below. Thus, the leached portion 554 has been leached to the intermediate leaching depth 553. However, as previously mentioned above, one or more by-product materials 398 are formed and deposited within some of the interstitial spaces 212 (FIG. 2) in the leached portion 554 during the leaching process. These by-product materials 398 are chemical by-products, or catalyst salts, of the dissolution reaction which are trapped within the open porosity of the interstitial spaces 212 (FIG. 2) during and/or after the dissolution process has been completed. Further, these trapped by-product materials 398 cause the leaching rate to decrease as the concentration of by-product materials 398 within the leached portion 554 increases. The unleached layer 556 is composed similarly as the PCD cutting table 150 (FIG. 1) and extends from a leaching depth end 555 of the leached portion 554 to the opposing surface 514. In the unleached layer 556, the cobalt 214 remains within the interstitial spaces 212 (FIG. 2) and has not been removed. Although the leaching depth end 555 is depicted as being substantially linear, the leaching depth end 555 can be non-linear.

The leaching process is performed a first time and removes at least a portion of the catalyst materials 214 from the PDC cutter 100 (FIG. 1) to form the intermediately leached PDC cutter 500. The leaching process is performed using a catalyst removal apparatus according to some exemplary embodiments. There are several catalyst removal apparatuses that are known or not yet known to people having ordinary skill in the art which are applicable to the present disclosure. For example, one such catalyst removal apparatus (not shown) includes a tank (not shown), or tray, having a cavity (not shown) formed therein and an acid solution (not shown) placed within the cavity. This apparatus is operated using the conventional leaching process described above according to some exemplary embodiments and is not repeated again for the sake of brevity. Other examples of the catalyst removal apparatus include, but are not limited to, at least those apparatuses which utilize acid leaching processes and/or electrochemical removal processes.

Referring back to FIG. 4, the leaching method 400 proceeds to step 440. At step 440, a cleaning process is performed on the leached portion 554 (FIG. 5) of the intermediately leached PDC cutter 500 (FIG. 5). The cleaning process removes at least a portion of the by-product materials 398 (FIG. 5) from the leached portion 554 (FIG. 5) of the polycrystalline structure 510 (FIG. 5). At step 440, an intermediately cleaned leached PDC cutter 600 (FIG. 6) is formed from the intermediately leached PDC cutter 500 (FIG. 5) where at least some of the by-product materials 398 (FIG. 5) has been removed.

Figure 6:
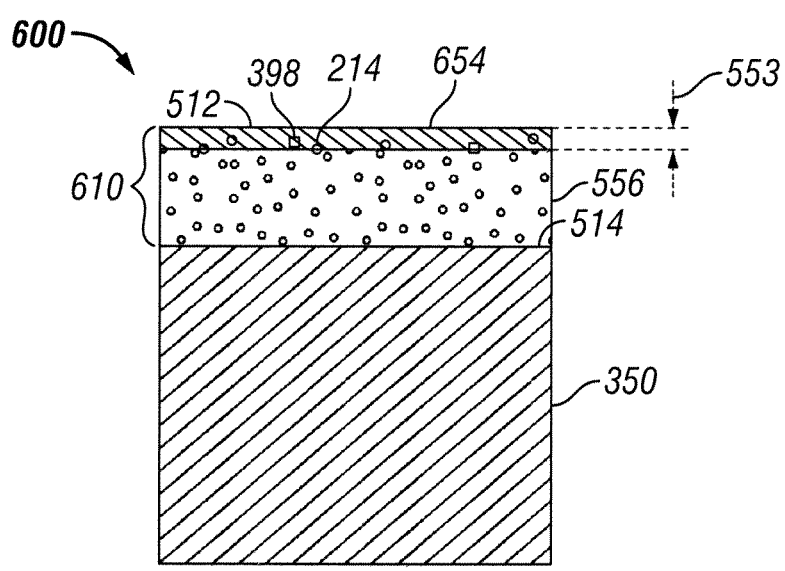
FIG. 6 shows a cross-sectional view of the intermediately cleaned leached PDC cutter in accordance with an exemplary embodiment of the present invention.

FIG. 6 shows a cross-sectional view of the intermediately cleaned leached PDC cutter 600 in accordance with an exemplary embodiment of the present invention. Referring to FIG. 6, the intermediately cleaned leached PDC cutter 600 includes the PCD cutting table 610 coupled to the substrate 350. The substrate 350 has been previously described with respect to FIG. 3 and is not described again for the sake of brevity. The PCD cutting table 610 is similar to the PCD cutting table 510 (FIG. 5), but includes a cleaned leached portion 654 that has had at least a portion of the by-product materials 398 removed from the leached portion 554 (FIG. 5). Thus, PCD cutting table 610 includes the cleaned leached portion 654 and the unleached layer 556 which is disposed between the cleaned leached portion 654 and the substrate 350. The cleaned leached portion 654 extends from the cutting surface 512, which has been described above with respect to FIG. 5, towards the opposing surface 514, which also has been described with respect to FIG. 5. In the cleaned leached portion 654, at least a portion of the cobalt 214 has been removed from within the interstitial spaces 212 (FIG. 2) using at least one leaching process mentioned above when compared to the PCD cutting table 110 (FIG. 1). Thus, the cleaned leached portion 654 has been leached to the intermediate leaching depth 553. However, as previously mentioned above, one or more by-product materials 398 were formed and deposited within some of the interstitial spaces 212 (FIG. 2) in the leached portion 554 (FIG. 5) during the leaching process. However, at least a portion of these by-product materials 398 are removed from the leached portion 554 (FIG. 5), thereby forming cleaned leached portion 654 of the intermediately cleaned leached PDC cutter 600. The process of removing the by-product materials 398 from the leached portion 554 (FIG. 5) is described in further detail below. As previously mentioned, these by-product materials 398 are chemical by-products, or catalyst salts, of the dissolution reaction which are trapped within the open porosity of the interstitial spaces 212 (FIG. 2) after the dissolution process has been completed. The unleached layer 556 has been previously described with respect to FIG. 5 and therefore is not repeated for the sake of brevity.

Figure 7:
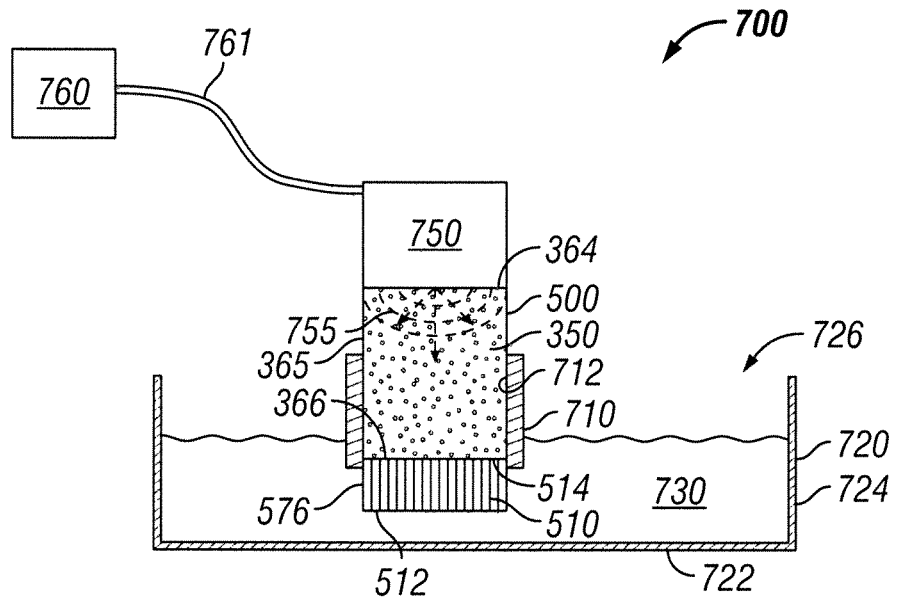
FIG. 7 is a cross-sectional view of a by-products removal apparatus in accordance with an exemplary embodiment.

The cleaning process is performed a first time and removes the by-product materials from the leached portion 554 (FIG. 5) of the intermediately leached PDC cutter 500 (FIG. 5) to form the intermediately cleaned leached PDC cutter 600. The cleaning process continues until a desired cleaning level is determined, which is determined by a user. Alternatively, the cleaning process continues for a desired cleaning period, which also is determined by the user. The desired cleaning period ranges from a few minutes to several hours or days, if desired. PLEASE PROVIDE TIME PERIODS IF AVAILABLE. The cleaning process is performed using a by-products removal apparatus according to some exemplary embodiments. There are several by-products removal apparatuses that are known or not yet known to people having ordinary skill in the art which are applicable to the present disclosure. For example, FIG. 7 is a cross-sectional view of a by-products removal apparatus 700 in accordance with an exemplary embodiment. Referring to FIG. 7, the by-products removal apparatus 700 includes the intermediately leached PDC cutter 500, a covering 710, an immersion tank 720, a cleaning fluid 730, a transducer 750, and at least one power source 760. According to certain exemplary embodiments, the covering 710 is optional. As the cleaning fluid 730 becomes increasingly more basic or more acidic, the use of the covering 710 becomes less optional.

The intermediately leached PDC cutter 500 has been previously described with respect to FIG. 5 and therefore is not described again in detail. Referring to FIGS. 5 and 7, the intermediately leached PDC cutter 500 includes the PCD cutting table 510 and the substrate 350 that is coupled to the PCD cutting table 510. As previously mentioned, the PCD cutting table 510 includes the leached portion 554 and the unleached layer 556 disposed between the leached portion 554 and the substrate 350. The leached portion 554 has at least a portion of the catalyst material 214 removed from therein using a known leaching process or some other process for removing the catalyst material 214. The leached portion 554 also includes by-product materials 398, which has been discussed in detail above and is not repeated again for the sake of brevity. The unleached layer 556 includes catalyst material 214 which has not been removed. Although the PCD cutting table 510 is used in the exemplary embodiment, other types of cutting tables, including PCBN compacts, are used in alternative exemplary embodiments. The PCD cutting table 510 is about one hundred thousandths of an inch (2.5 millimeters) thick; however, the thickness is variable depending upon the application in which the PCD cutting table 510 is to be used. Also, although the intermediately leached PDC cutter 500 is described as being used in the by-products removal apparatus 700, the leached PDC cutter 300 (FIG. 3) can be used in certain exemplary embodiments.

Referring to FIGS. 5 and 7 and as previously mentioned, the by-products removal apparatus 700 includes the covering 710, which is optional. In certain exemplary embodiments, the covering 710 is annularly shaped and forms a channel 712 therein. The covering 710 surrounds at least a portion of a substrate outer wall 366 extending from about the perimeter of a top surface 365 of the substrate 350 towards a bottom surface 364 of the substrate 350. The bottom surface 364, the top surface 365, and the substrate outer wall 366 of substrate 350 are similar to the bottom surface 154 (FIG. 1), the top surface 152 (FIG. 1), and the substrate outer wall 156 (FIG. 1), respectively, of the substrate 150 (FIG. 1) and is not repeated herein again. In some exemplary embodiments, a portion of the covering 710 also surrounds a portion of the perimeter of a PCD cutting table outer wall 576 extending from the perimeter of the opposing surface 514 towards the cutting surface 512. The PCD cutting table outer wall 576 of the intermediately leached PDC cutter 500 is similar to the PCD cutting table outer wall 116 (FIG. 1) of the PDC cutter 100 (FIG. 1) and therefore is not repeated again. Thus, the cutting surface 512 and at least a portion of the PCD cutting table outer wall 576 is exposed and not concealed by the covering 710 in certain exemplary embodiments. The covering 710 is fabricated using epoxy resin; however, other suitable materials, such as a plastic, porcelain, or Teflon®, can be used without departing from the scope and spirit of the exemplary embodiment. In some exemplary embodiments, the covering 710 is positioned around at least a portion of the intermediately leached PDC cutter 500 by inserting the intermediately leached PDC cutter 500 through the channel 712 of the covering 710. The covering 710 is friction fitted to the intermediately leached PDC cutter 500 in some exemplary embodiments, while in other exemplary embodiments, the covering 710 is securely positioned by placing an o-ring (not shown), or other suitable known device, around the intermediately leached PDC cutter 500 and inserting the intermediately leached PDC cutter 500 and the coupled o-ring into the covering 710 so that the o-ring is inserted into a circumferential groove (not shown) formed within the internal surface of the covering 710. In an alternative exemplary embodiment, the covering 710 is circumferentially applied onto the substrate outer wall 366 and/or the PCD cutting table outer wall 576 of the intermediately leached PDC cutter 500. Although some methods for securing the covering 710 to the intermediately leached PDC cutter 500 have been described, other methods known to people having ordinary skill in the art can be used without departing from the scope and spirit of the exemplary embodiment. The covering 710 protects the surface of the substrate outer wall 366 and/or at least a portion of the PCD cutting table outer wall 576 to which it is applied from being exposed to the cleaning fluid 730, which is discussed in further detail below.

The immersion tank 720 includes a base 722 and a surrounding wall 724 extending substantially perpendicular around the perimeter of the base 722, thereby forming a cavity 726 therein. According to certain exemplary embodiments, the base 722 is substantially planar; however, the base 722 is non-planar in other exemplary embodiments. Also in alternative exemplary embodiments, the surrounding wall 724 is non-perpendicular to the base 722. Also, the immersion tank 720 is formed having a rectangular shape. Alternatively, the immersion tank 720 is formed having any other geometric shape or non-geometric shape. In some exemplary embodiments, the immersion tank 720 is fabricated using a plastic material; however, other suitable materials, such as metal, metal alloys, or glass, are used in other exemplary embodiments. The material used to fabricate the immersion tank 720 typically does not react with the cleaning fluid 730. According to some exemplary embodiments, a removable lid (not shown) is used to enclose at least the intermediately leached PDC cutter 500 and the transducer 750, thereby providing a seal to the cavity 730. Hence, the removable lid and the immersion tank 720 together form a pressurized vessel (not shown). In these exemplary embodiments, the power source 760 can be coupled to the lid, can be positioned outside the pressurized vessel as long as the pressurized vessel provides a port (not shown) to electrically couple the power source 760 to the transducer 750, or can be integrated with the transducer 750.

The cleaning fluid 730 is placed within the cavity 726 of the immersion tank 720 and filled to a depth of at least the thickness of the PCD cutting table 710. The cleaning fluid 730 is de-ionized water in the exemplary embodiment. The by-product materials 398 that clog the PCD open porosity is dissolvable in the cleaning fluid 730. According to some exemplary embodiments, one or more additional chemicals are added to the de-ionized water to form the cleaning fluid 730 and increase the rate at which the by-product materials 398 are dissolved into the cleaning fluid 730. These additional chemicals are based upon the composition of the by-product materials 398. Some examples of these additional chemicals are acetic acid and/or formic acid to make the solution slightly acidic or ammonia to make the solution slightly basic. However, in other exemplary embodiments, any fluid or solution that is able to dissolve and/or react with the by-product materials 398 can be used for the cleaning fluid 730 in lieu of, or in addition to, the de-ionized water. According to some exemplary embodiments, the cleaning fluid 730 is heated to increase the rate at which the by-product materials 398 are dissolved into the cleaning fluid 730 and hence accelerate the cleaning process. The temperature of the cleaning fluid 730 can be heated up to 100° C. in the immersion tank 720 or some similar type tank. However, the temperature of the cleaning fluid 730 can be heated higher than 100° C. in the pressurized vessel mentioned above, thereby avoiding or reducing boiling of the cleaning fluid 730.

The transducer 750 is coupled to the intermediately leached PDC cutter 500 according to some exemplary embodiments. According to some exemplary embodiments, a portion of the transducer 750 is coupled to the bottom surface 364 of the intermediately leached PDC cutter 500; however the transducer 750 can be coupled to a portion of the substrate outer wall 366 in other exemplary embodiments. Alternatively, the transducer 750 is coupled to a portion of the immersion tank 720 or positioned within the cleaning fluid 730, thereby producing vibrations which propagate through the cleaning fluid 730 and into the intermediately leached PDC cutter 500. The transducer 750 also is coupled to a power source 760 using an electrical wire 761. The transducer 750 converts electric current supplied from the power source 760 into vibrations that are propagated through the intermediately leached PDC cutter 500. The transducer 750 is shaped into a cylindrical shape and has a circumference sized approximately similarly to the circumference of the bottom surface 364. However, the shape and size of the transducer 750 varies in other exemplary embodiments. The transducer 750 is a piezoelectric transducer; however, the transducer 750 is a magnetostrictive transducer in other exemplary embodiments. The transducer 750 operates at a frequency of about forty kilohertz (kHz) in some exemplary embodiments. In other exemplary embodiments, the transducer 750 operates at a frequency ranging from about twenty kHz to about fifty kHz; yet, in still other exemplary embodiments, the operating frequency is higher or lower than the provided range. The transducer 750 supplies ultrasonic vibrations 755 which propagate through the intermediately leached PDC cutter 500 and facilitate the by-product materials 398 removal from the interstitial spaces 212 (FIG. 2) formed within the PCD cutting table 510, which is further described below.

Figure 2:
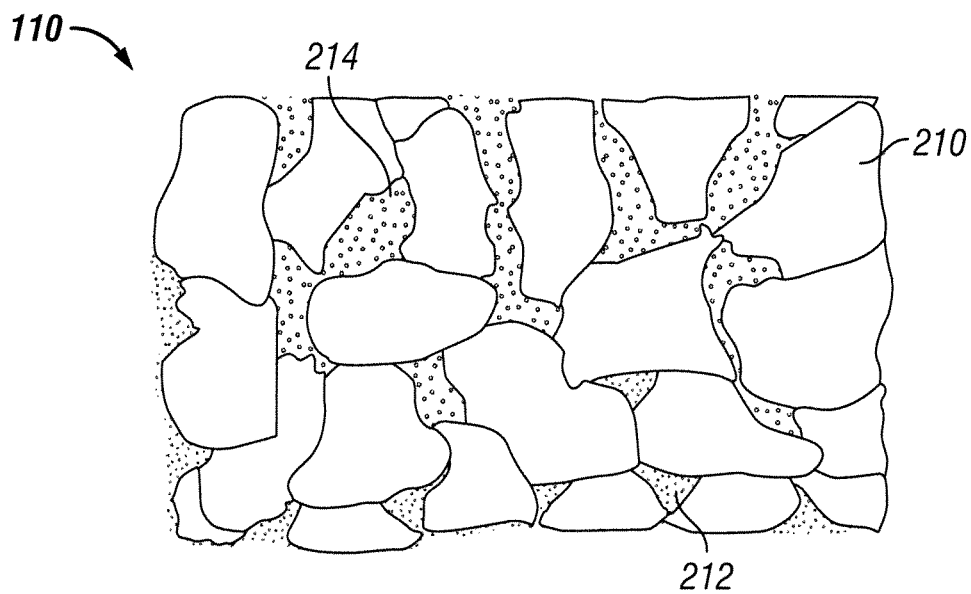
FIG. 2 is a schematic microstructural view of the PCD cutting table of FIG. 1 in accordance with the prior art.

Once the by-products removal apparatus 700 has been set up and at least a portion of the PCD cutting table 510 is immersed into the cleaning fluid 730, the cleaning fluid 730 penetrates into the leached portion 554 and dissolves the by-product materials 398 that are clogging the PCD open porosity. The by-product materials 398 are highly soluble in the cleaning fluid 730. In certain exemplary embodiments, the transducer 750 and the power source 760 are included in the by-product removal apparatus 700. The power source 760 is turned "on" to facilitate removal of the by-product materials 398 from the PCD cutting table 510 back into the cleaning fluid 730. The transducer 750 produces ultrasonic vibrations 755 into the intermediately leached PDC cutter 500 which promotes the removal of the by-product materials 398 from the PCD cutting table 510 back into the cleaning fluid 730. The operating frequency of the transducer 750 and the intensity of the elastic waves emitted from the transducer 750 can be adjusted to maximize the amount of vibrations 755 delivered to the PCD cutting table 510. Furthermore, the ultrasonic vibrations 755 mechanically improve the cleaning fluid 730 circulation rate into and out of the interstitial spaces 212 (FIG. 2), thereby providing fresh cleaning fluid 730 into the interstitial spaces 212 (FIG. 2). Once the by-product material 398 is removed from the PCD cutting table 510, the cleaning fluid 730 is able to proceed deeper into the PCD cutting table 510 and dissolve more by-product materials 398 located within additional interstitial voids 212 (FIG. 2). Upon at least some of the by-product materials 398 being removed from the leached portion 554, the intermediately leached PDC cutter 500 becomes the intermediately cleaned leached PDC cutter 600 (FIG. 6). Although a single intermediately leached PDC cutter 500 is shown to be immersed in the cleaning fluid 730, several intermediately leached PDC cutters 500 can be immersed into the cleaning fluid 730 to remove the by-product materials 398 from each of the PCD cutting tables 510 simultaneously in other exemplary embodiments.

Figure 8:
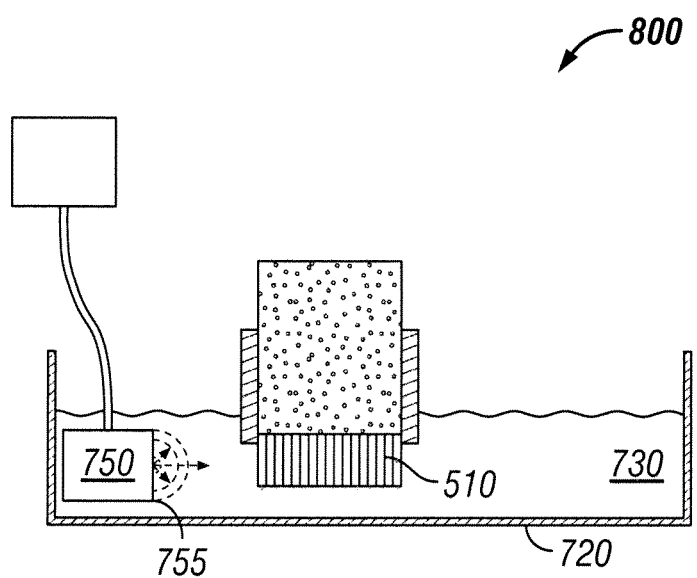
FIG. 8 is a cross-sectional view of a by-products removal apparatus in accordance with another exemplary embodiment.

In another example, FIG. 8 is a cross-sectional view of a by-products removal apparatus 800 in accordance with another exemplary embodiment. The by-products removal apparatus 800 is similar to the by-products removal apparatus 700 (FIG. 7) except that the transducer 750 of the by-products removal apparatus 800 is submerged within the cleaning fluid 730. The transducer 750 transmits ultrasonic vibrations 755 into the cleaning fluid 730, which then transmits the vibrations 755 into the PCD cutting table 510. As previously mentioned, the ultrasonic vibrations 755 facilitate removal of the by-product materials 398, or salt, within the interstitial void 212 (FIG. 2) and increase the recirculation rate of the fresh cleaning fluid 730 into the PCD cutting table 510. Thus, the by-product material 398 removal rate is substantially increased using the transducer 750. Alternatively, the transducer 750 is coupled to a portion of the immersion tank 720. The other exemplary embodiments and/or modifications as described with respect to FIG. 7 above are applicable to the present exemplary embodiment.

Figure 9:
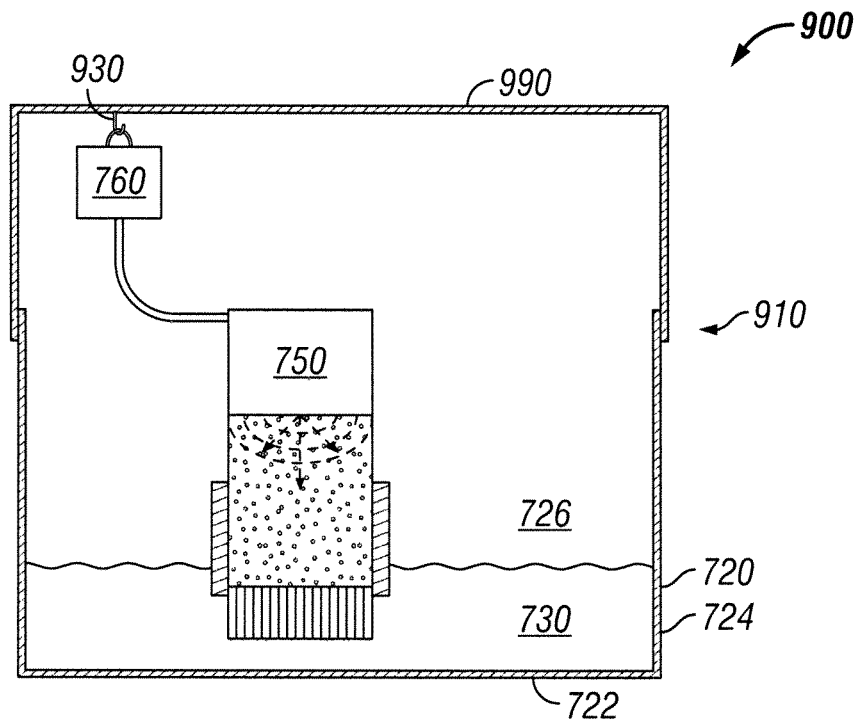
FIG. 9 is a cross-sectional view of a by-products removal apparatus in accordance with another exemplary embodiment.

In another example, FIG. 9 is a cross-sectional view of a by-products removal apparatus 900 in accordance with another exemplary embodiment. The by-products removal apparatus 900 is similar to the by-products removal apparatus 700 (FIG. 7) except that the cavity 726 of the immersion tank 720 is covered by a lid 990 in the by-products removal apparatus 900. In certain exemplary embodiments, the lid 990 provides a seal to the cavity 726, thereby allowing the cavity 726 to be pressurized and the cleaning fluid 730 to be heated at higher temperatures, such as above 100° C. These higher temperatures increase the cleaning rate of the by-products materials 398 (FIG. 5). A gasket (not shown) positioned between the lid 990 and the immersion tank 720 can be used to facilitate providing the seal. The sealed lid 990 and the immersion tank 720 collectively form the pressurizable vessel 910. In the exemplary embodiments that use the lid 990, the power source 760 can be coupled to the lid 990 via a clamp 930, can be positioned outside the pressurizable vessel 910 as long as the pressurized vessel 910 provides a port (not shown) to electrically couple the power source 760 to the transducer 750, or can be integrated with the transducer 750. The other exemplary embodiments and/or modifications as described with respect to FIG. 7 above are applicable to the present exemplary embodiment.

Figure 10:
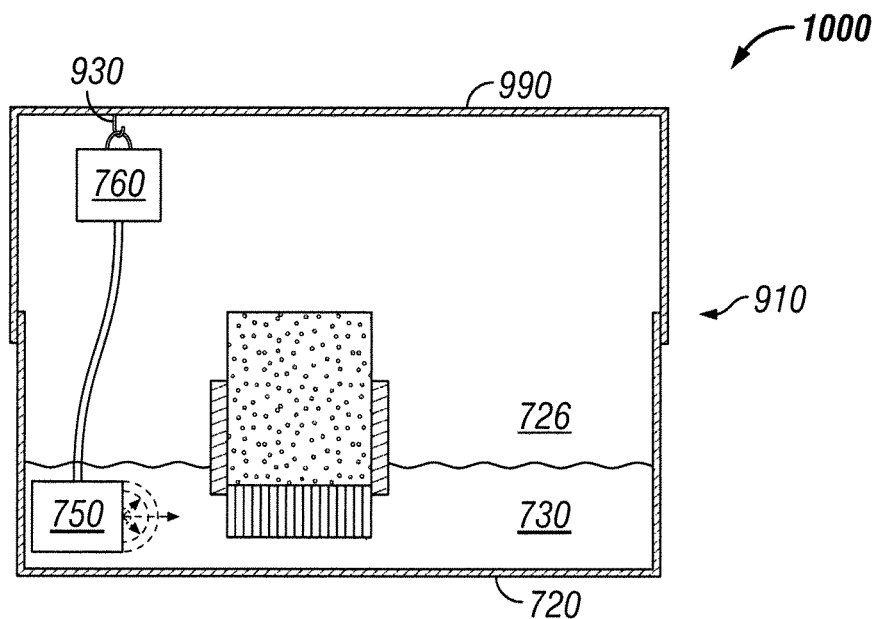
FIG. 10 is a cross-sectional view of a by-products removal apparatus in accordance with another exemplary embodiment.

In yet another example, FIG. 10 is a cross-sectional view of a by-products removal apparatus 1000 in accordance with another exemplary embodiment. The by-products removal apparatus 1000 is similar to the by-products removal apparatus 800 (FIG. 8) except that the cavity 726 of the immersion tank 720 is covered by a lid 990 in the by-products removal apparatus 1000. In certain exemplary embodiments, the lid 990 provides a seal to the cavity 726, thereby allowing the cavity 726 to be pressurized and the cleaning fluid 730 to be heated at higher temperatures, such as above 100° C. These higher temperatures increase the cleaning rate of the by-products materials 398 (FIG. 5). A gasket (not shown) positioned between the lid 990 and the immersion tank 720 can be used to facilitate providing the seal. The sealed lid 990 and the immersion tank 720 collectively form the pressurizable vessel 910. In the exemplary embodiments that use the lid 990, the power source 760 can be coupled to the lid 990 via a clamp 930, can be positioned outside the pressurizable vessel 910 as long as the pressurized vessel 910 provides a port (not shown) to electrically couple the power source 760 to the transducer 750, or can be integrated with the transducer 750. The other exemplary embodiments and/or modifications as described with respect to FIG. 7 and above are applicable to the present exemplary embodiment.

Figure 11:
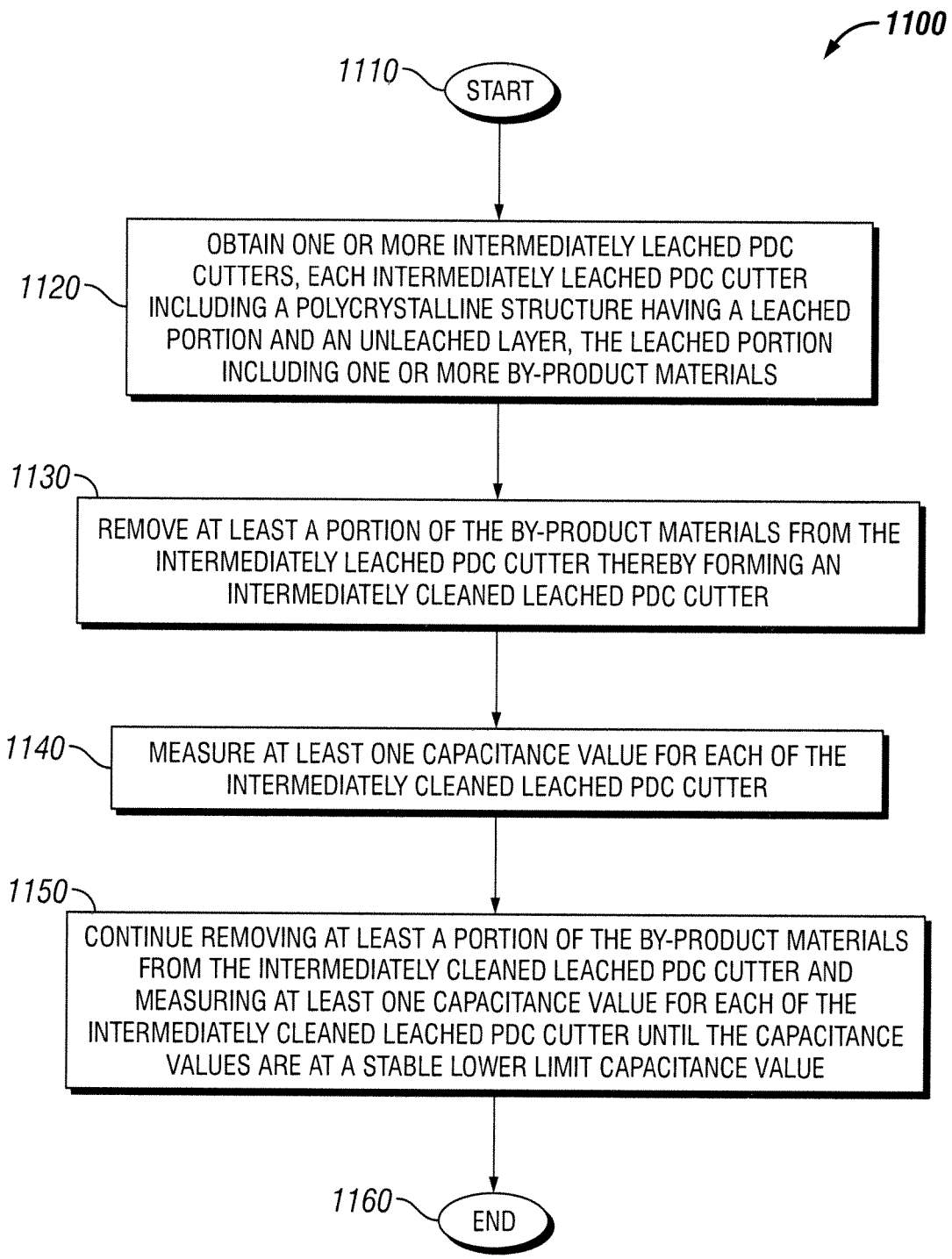
FIG. 11 is a flowchart depicting a by-product materials removal verification method in accordance with an exemplary embodiment of the present invention.

According to some exemplary embodiments, the effectiveness of the by-product materials removal process is optionally verified. In the event that the intermediately cleaned leached PDC cutter 600 is not cleaned to a desired level, the intermediately cleaned leached PDC cutter 600 is further cleaned in either the same cleaning fluid 730 or a fresh cleaning fluid 730 until the desired level is reached. Thus, multiple cleaning cycles are performed on the intermediately leached PDC cutter 500 in some exemplary embodiments to fully, or substantially, remove the by-product materials 398. FIG. 11 is a flowchart depicting a by-product materials removal verification method 1100 in accordance with an exemplary embodiment of the present invention. Although FIG. 11 shows a series of steps depicted in a certain order, the order of one or more steps can be rearranged, combined into fewer steps, and/or separated into more steps than that shown in other exemplary embodiments. Referring to FIG. 11, the by-product materials removal verification method 1100 begins at step 1110. Upon starting at step 1110, the by-product materials removal verification method 1100 proceeds to step 1120. At step 1120, one or more intermediately leached PDC cutters are obtained. According to certain exemplary embodiments, each intermediately leached PDC cutter includes a polycrystalline structure having a leached portion and an unleached layer. The leached portion includes one or more by-product materials. These intermediately leached PDC cutters have been described above in detail with respect to FIG. 5 and therefore are not described again for the sake of brevity.

The by-product materials removal verification method 1100 proceeds to step 1130. At step 1130, at least a portion of the by-product materials from the intermediately leached PDC cutter is removed thereby forming an intermediately cleaned leached PDC cutter. The by-product materials are removed from the intermediately leached PDC cutter using the by-products removal apparatus 700 (FIG. 7), the by-products removal apparatus 800 (FIG. 8), the by-products removal apparatus 900 (FIG. 9), the by-products removal apparatus 1000 (FIG. 10), or some other by-products removal apparatus that becomes known to other people having ordinary skill in the art with the benefit of the present disclosure. As previously described, a cleaning fluid and a transducer, according to some exemplary embodiments, are used to remove at least a portion of the by-product materials from the intermediately leached PDC cutter.

The by-product materials removal verification method 1100 proceeds to step 1140. At step 1140, at least one capacitance value for each of the intermediately cleaned leached PDC cutter is measured. The intermediately cleaned leached PDC cutter has been described above in detail with respect to FIG. 6 and therefore is not described again for the sake of brevity. The capacitance value is determined using a capacitance measuring system, as described below.

Figure 12:
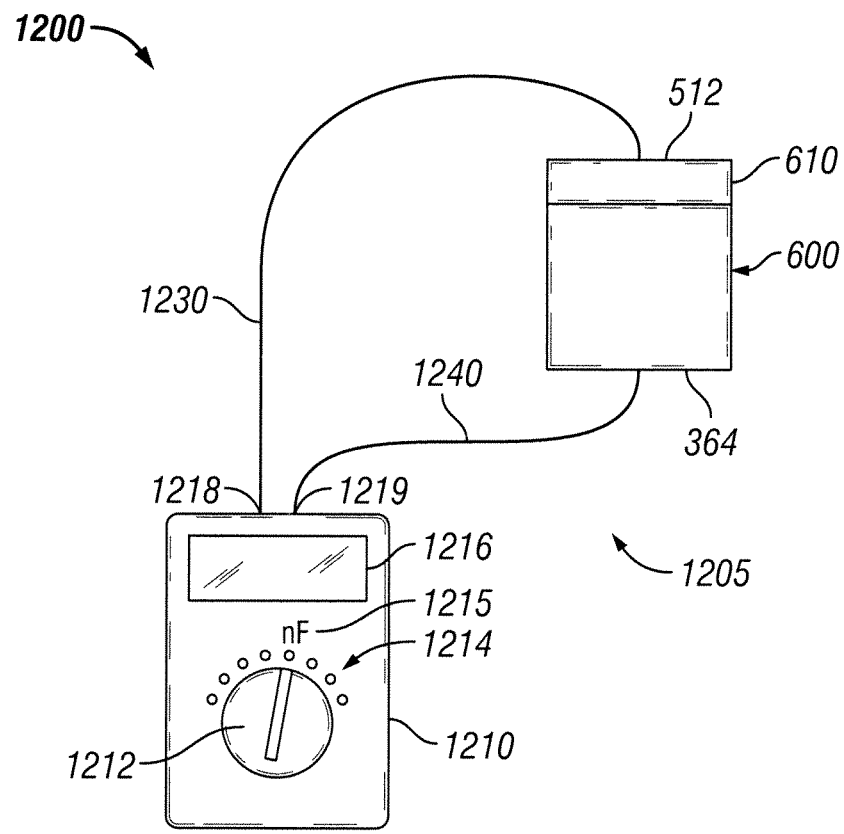
FIG. 12 is a schematic view of a capacitance measuring system in accordance to one exemplary embodiment of the present invention.

FIG. 12 is a schematic view of a capacitance measuring system 1200 in accordance to one exemplary embodiment of the present invention. Referring to FIG. 12, the capacitance measuring system 1200 includes a capacitance measuring device 1210, the intermediately cleaned leached PDC cutter 600, a first wire 1230, and a second wire 1240. In other exemplary embodiments, the intermediately leached PDC cutter 500 (FIG. 5) is used in lieu of the intermediately cleaned leached PDC cutter 600. Although certain components have been enumerated as being included in the capacitance measuring system 1200, additional components are included in other exemplary embodiments. Additionally, although the description provided below has been provided with respect to the intermediately cleaned leached PDC cutter 600, a different component, such as the PCD cutting table 610 alone or other component that includes another type of intermediately clean leached polycrystalline structure or intermediately leached polycrystalline structure, is used in lieu of the intermediately cleaned leached PDC cutter 600. The cleaned leached PDC cutter 600 has been previously described with respect to FIG. 6 and is not repeated again herein for the sake of brevity.

The capacitance measuring device 1210 is a device that measures the capacitance of an energy storage device, which is the intermediately cleaned leached PDC cutter 600, or the intermediately leached PDC cutter 500 (FIG. 5), in the instant exemplary embodiment. Capacitance is a measure of the amount of electric potential energy stored, or separated, for a given electric potential. A common form of energy storage device is a parallel-plate capacitor. In the instant exemplary embodiment, the intermediately cleaned leached PDC cutter 600 is an example of the parallel-plate capacitor. The capacitance of the energy storage device is typically measured in farads, or nanofarads.

One example of the capacitance measuring device 1210 is a multi-meter; however, other capacitance measuring devices known to people having ordinary skill in the art are used in one or more alternative exemplary embodiments. The multi-meter 1210 includes a positionable dial 1212, a plurality of measurement settings 1214, a display 1216, a positive terminal 1218, and a negative terminal 1219. According to some exemplary embodiments, the positionable dial 1212 is rotatable in a clockwise and/or counter-clockwise manner and is set to one of several available measurement settings 1214. In the instant exemplary embodiment, the positionable dial 1212 is set to a nanofaraday setting 1215 so that the multi-meter 1210 measures capacitance values. The display 1216 is fabricated using polycarbonate, glass, plastic, or other known suitable material and communicates a measurement value, such as a capacitance value, to a user (not shown) of the multi-meter 1210. The positive terminal 1218 is electrically coupled to one end of the first wire 1230, while the negative terminal 1219 is electrically coupled to one end of the second wire 1240.

The first wire 1230 is fabricated using a copper wire or some other suitable conducting material or alloy known to people having ordinary skill in the art. According to some exemplary embodiments, the first wire 1230 also includes a non-conducting sheath (not shown) that surrounds the copper wire and extends from about one end of the copper wire to an opposing end of the cooper wire. The two ends of the copper wire are exposed and are not surrounded by the non-conducting sheath. In some exemplary embodiments, an insulating material (not shown) also surrounds the copper wire and is disposed between the copper wire and the non-conducting sheath. The insulating material extends from about one end of the non-conducting sheath to about an opposing end of the non-conducting sheath. As previously mentioned, one end of the first wire 830 is electrically coupled to the positive terminal 1218, while the opposing end of the first wire 1230 is electrically coupled to the cutting surface 512 of the intermediately cleaned leached PDC cutter 600. The opposing end of the first wire 1230 is electrically coupled to the cutting surface 512 in one of several methods. In one example, the first wire 1230 is electrically coupled to the cutting surface 512 using one or more fastening devices (not shown), such as a clamp, or using an equipment (not shown) that supplies a force to retain the first wire 1230 in electrical contact with the cutting surface 512. In another example, a clamp (not shown) is coupled to the opposing end of the first wire 1230 and a conducting component (not shown), such as aluminum foil, is coupled to, or placed in contact with, the cutting surface 512. The clamp is electrically coupled to the conducting component, thereby electrically coupling the first wire 1230 to the cutting surface 512. Additional methods for coupling the first wire 1230 to the cutting surface 512 can be used in other exemplary embodiments.

The second wire 1240 is fabricated using a copper wire or some other suitable conducting material or alloy known to people having ordinary skill in the art. According to some exemplary embodiments, the second wire 1240 also includes a non-conducting sheath (not shown) that surrounds the copper wire and extends from about one end of the copper wire to an opposing end of the cooper wire. The two ends of the copper wire are exposed and are not surrounded by the non-conducting sheath. In some exemplary embodiments, an insulating material (not shown) also surrounds the copper wire and is disposed between the copper wire and the non-conducting sheath. The insulating material extends from about one end of the non-conducting sheath to an opposing end of the non-conducting sheath. As previously mentioned, one end of the second wire 1240 is electrically coupled to the negative terminal 1219, while the opposing end of the second wire 1240 is electrically coupled to a bottom surface 364, which is similar to the bottom surface 154 (FIG. 1), of the intermediately cleaned leached PDC cutter 600. The second wire 1240 is electrically coupled to the bottom surface 364 in a similar manner as the first wire 1230 is electrically coupled to the cutting surface 512.

Hence, a circuit 1205 is completed using the multi-meter 1210, the first wire 1230, the intermediately cleaned leached PDC cutter 600, and the second wire 1240. The current is able to flow from the positive terminal 1218 of the multi-meter 1210 to the cutting surface 512 of the intermediately cleaned leached PDC cutter 600 through the first wire 1230. The current then flows through the intermediately cleaned leached PDC cutter 600 to the bottom surface 364 of the intermediately cleaned leached PDC cutter 600. When the multi-meter 1210 is turned on, a voltage differential exists between the cutting surface 512 and the bottom surface 364. The current then flows from the bottom surface 364 to the negative terminal 1219 of the multi-meter 1210 through the second wire 1240. The capacitance measurement of the intermediately cleaned leached PDC cutter 600 is determined when the value displayed on the display 1216 reaches a peak value or remains constant for a period of time. The use, analyzing of the results, and other information regarding the capacitance measuring system 1200 is described in U.S. patent application Ser. No. 13/401,188, entitled "Use of Capacitance to Analyze Polycrystalline Diamond" and filed on Feb. 21, 2012, which has been incorporated by reference herein.

Figure 13:
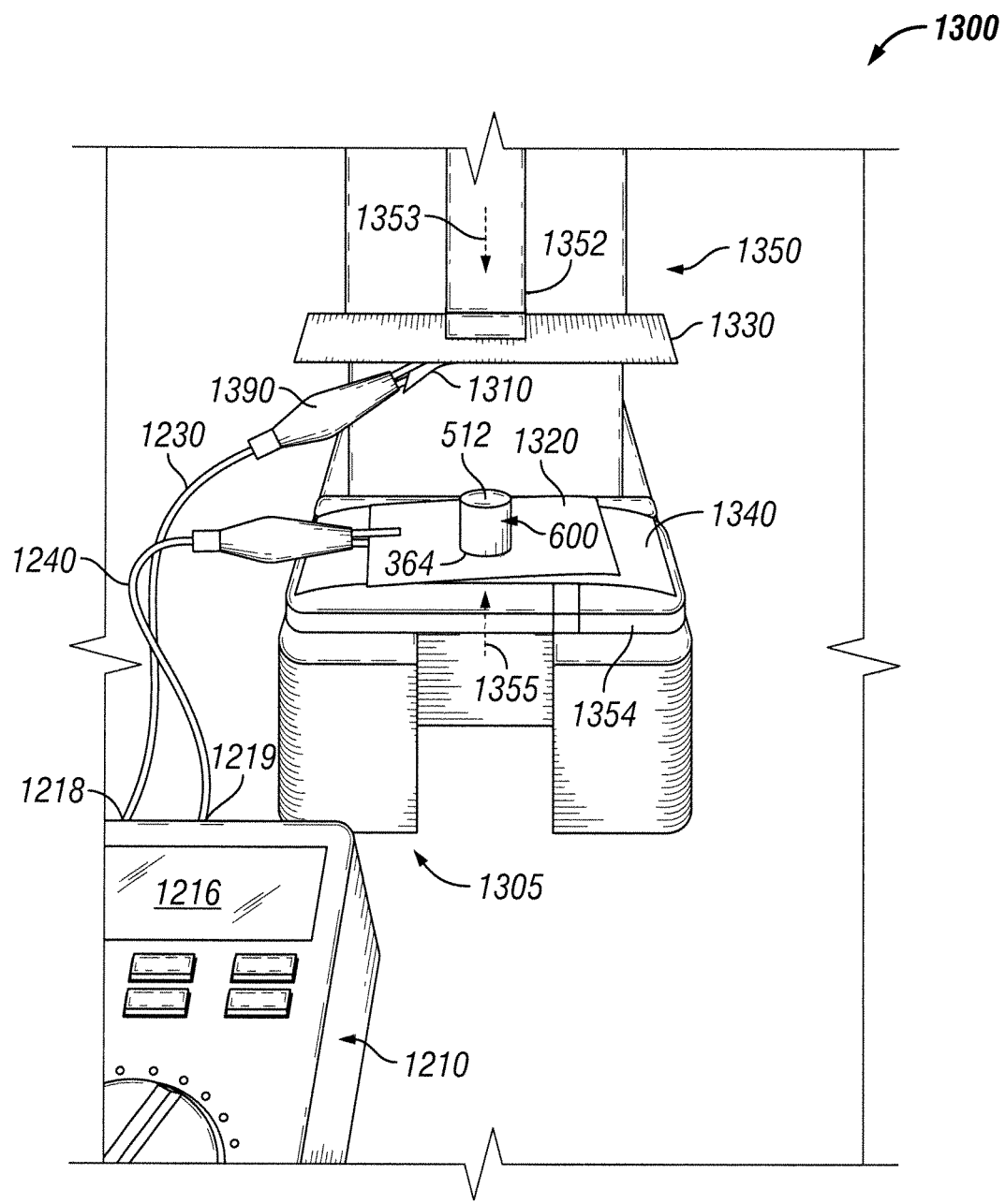
FIG. 13 is a schematic view of a capacitance measuring system in accordance to another exemplary embodiment of the present invention.

FIG. 13 is a schematic view of a capacitance measuring system 1300 in accordance to another exemplary embodiment of the present invention. Referring to FIG. 13, the capacitance measuring system 1300 includes the capacitance measuring device 1210, the intermediately cleaned leached PDC cutter 600, the first wire 1230, the second wire 1240, a first conducting material 1310, a second conducting material 1320, a first insulating material 1330, a second insulating material 1340, and an Arbor Press 1350. In certain alternative exemplary embodiments, the intermediately leached PDC cutter 500 (FIG. 5) is used in lieu of the intermediately cleaned leached PDC cutter 600. Although certain components have been enumerated as being included in the capacitance measuring system 1300, additional components are included in other exemplary embodiments. Further, although certain components have been enumerated as being included in the capacitance measuring system 1300, alternative components having similar functions as the enumerated components are used in alternative exemplary embodiments. Additionally, although the description provided below has been provided with respect to the intermediately cleaned leached PDC cutter 600, a different component, such as the PCD cutting table 610 (FIG. 6) alone or other component that includes another type of leached, or cleaned leached, polycrystalline structure, is used in lieu of the intermediately cleaned leached PDC cutter 600. The capacitance measuring device 1210, the intermediately cleaned leached PDC cutter 600, the first wire 1230, and the second wire 1240 have been previously described and are not repeated again herein for the sake of brevity.

The first conducting material 1310 and the second conducting material 1320 are similar to one another in certain exemplary embodiments, but are different in other exemplary embodiments. According to one exemplary embodiment, the conducting materials 1310, 1320 are fabricated using aluminum foil; however, other suitable conducting materials can be used. The first conducting material 1310 is positioned adjacently above and in contact with the cutting surface 512. The second conducting material 1320 is positioned adjacently below and in contact with the bottom surface 364. The first conducting material 1310 and the second conducting material 1320 provide an area to which the first wire 1230 and the second wire 1240, respectively, make electrical contact. Additionally, the first conducting material 1310 and the second conducting material 1320 assist in minimizing contact resistance with the cutting surface 512 and the bottom surface 364, respectively, which is discussed in further detail below. In certain exemplary embodiments, the first conducting material 1310 and the second conducting material 1320 are the same shape and size; while in other exemplary embodiments, one of the conducting materials 1310, 1320 is a different shape and/or size than the other conducting material 1310, 1320.

The first insulating material 1330 and the second insulating material 1340 are similar to one another in certain exemplary embodiments, but are different in other exemplary embodiments. According to one exemplary embodiment, the insulating materials 1330, 1340 are fabricated using paper; however, other suitable insulating materials, such as rubber, can be used. The first insulating material 1330 is positioned adjacently above and in contact with the first conducting material 1310. The second insulating material 1340 is positioned adjacently below and in contact with the second conducting material 1320. The first insulating material 1330 and the second insulating material 1340 provide a barrier to direct current flow only through a circuit 1305, which is discussed in further detail below. In certain exemplary embodiments, the first insulating material 1330 and the second insulating material 1340 are the same shape and size; while in other exemplary embodiments, one of the insulating materials 1330, 1340 is a different shape and/or size than the other insulating material 1330, 1340. Additionally, in certain exemplary embodiments, the insulating materials 1330, 1340 is larger in size than its corresponding conducting material 1310, 1320. However, one or more of the insulating materials 1330, 1340 is either larger or smaller than its corresponding conducting material 1310, 1320 in alternative exemplary embodiments.

The Arbor Press 1350 includes an upper plate 1352 and a base plate 1354. The upper plate 1352 is positioned above the base plate 1354 and is movable towards the base plate 1354. In other exemplary embodiments, the base plate 1354 is movable towards the upper plate 1352. The first insulating material 1330, the first conducting material 1310, the intermediately cleaned leached PDC cutter 600, the second conducting material 1320, and the second insulating material 1340 are positioned between the upper plate 1352 and the base plate 1354 such that the second insulating material 1340 is positioned adjacently above and in contact with the base plate 1354. The upper plate 1352 is moved towards the base plate 1354 until the upper plate 1352 applies a downward load 1353 onto the cutting surface 512 of the intermediately cleaned leached PDC cutter 600. When the downward load 1353 is applied, the first conducting material 1310 is deformed and adapted to the rough and very stiff cutting surface 512, thereby minimizing contact resistance between the first conducting material 1310 and the cutting surface 512 and greatly improving the capacitance measurement consistency. At this time, the base plate 1354 also applies an upward load 1355 onto the bottom surface 364 of the intermediately cleaned leached PDC cutter 600. When the upward load 1355 is applied, the second conducting material 1320 is deformed and adapted to the rough and very stiff bottom surface 364, thereby minimizing contact resistance between the second conducting material 1320 and the bottom surface 364 and greatly improving the capacitance measurement consistency. In certain exemplary embodiments, the downward load 1353 is equal to the upward load 1355. The downward load 1353 and the upward load 1355 is about one hundred pounds; however, these loads 1353, 1355 range from about two pounds to about a critical load. The critical load is a load at which the intermediately cleaned leached PDC cutter 600 is damaged when applied thereto.

In one exemplary embodiment, the second insulating material 1340 is positioned on the base plate 1354, the second conducting material 1320 is positioned on the second insulating material 1340, the intermediately cleaned leached PDC cutter 600 is positioned on the second conducting material 1320, the first conducting material 1310 is positioned on the intermediately cleaned leached PDC cutter 600, and the first insulating material 1330 is positioned on the first conducting material 1310. The upper plate 1352 is moved towards the first insulating material 1330 until the downward load 1353 is applied onto the intermediately cleaned leached PDC cutter 600. In an alternative exemplary embodiment, one or more components, such as the first insulating material 1330 and the first conducting material 1310, are coupled to the upper plate 1352 prior to the upper plate 1352 being moved towards the base plate 1354. Although an Arbor Press 1350 is used in the capacitance measuring system 1300, other equipment capable of delivering equal and opposite loads to each of the cutting surface 512 and the bottom surface 364 of the intermediately cleaned leached PDC cutter 600 can be used in other exemplary embodiments.

One end of the first wire 1230 is electrically coupled to the positive terminal 1218 of the multi-meter 1210, while the opposing end of the first wire 1230 is electrically coupled to the first conducting material 1310, which thereby becomes electrically coupled to the cutting surface 512 of the intermediately cleaned leached PDC cutter 600. In one exemplary embodiment, a clamp 1390 is coupled to the opposing end of the first wire 1230 which couples the first wire 1230 to the first conducting material 1310. One end of the second wire 1240 is electrically coupled to the negative terminal 1219 of the multi-meter 1210, while the opposing end of the second wire 1240 is electrically coupled to the second conducting material 1320, which thereby becomes electrically coupled to the bottom surface 364 of the intermediately cleaned leached PDC cutter 600. In one exemplary embodiment, a clamp (not shown), similar to clamp 1390, is coupled to the opposing end of the second wire 1240, which couples the second wire 1240 to the second conducting material 1320. Hence, the circuit 1305 is completed using the multi-meter 1210, the first wire 1230, the first conducting material 1310, the intermediately cleaned leached PDC cutter 600, the second conducting material 1320, and the second wire 1340. The current is able to flow from the positive terminal 1218 of the multi-meter 1210 to the cutting surface 512 of the intermediately cleaned leached PDC cutter 600 through the first wire 1230 and the first conducting material 1310. The current then flows through the intermediately cleaned leached PDC cutter 600 to the bottom surface 364 of the intermediately cleaned leached PDC cutter 600. When the multi-meter 1210 is turned on, a voltage differential exists between the cutting surface 512 and the bottom surface 364. The current then flows from the bottom surface 364 to the negative terminal 1219 of the multi-meter 1210 through the second conducting material 1320 and the second wire 1240. The first insulating material 1330 and the second insulating material 1340 prevent the current from flowing into the Arbor Press 1350. The capacitance measurement of the intermediately cleaned leached PDC cutter 600 is determined when the value displayed on the display 1216 reaches a peak value or remains constant for a period of time. The use, analyzing of the results, and other information regarding the capacitance measuring system 1300 is described in U.S. patent application Ser. No. 13/401,188, entitled "Use of Capacitance to Analyze Polycrystalline Diamond" and filed on Feb. 21, 2012, which has been incorporated by reference herein.

Referring back to FIG. 11, the by-product materials removal verification method 1100 proceeds to step 1150. At step 1150, removal of at least a portion of the by-product materials from the intermediately cleaned leached PDC cutter and measuring at least one capacitance value for at least one of the intermediately cleaned leached PDC cutter is continued until the capacitance value is at a stable lower limit capacitance value. The removal of at least a portion of the by-product materials has been described with respect to step 1130 and the measuring of the capacitance values has been described with respect to step 1140. The stable lower limit capacitance value is the capacitance value of an intermediately cleaned leached PDC cutter at which the measured capacitance value does not further decrease upon further removal of by-product materials from the intermediately cleaned leached PDC cutter, i.e. further cleaning of the intermediately cleaned leached PDC cutter. The stable lower limit capacitance value is illustrated in FIG. 14.

Figure 14:
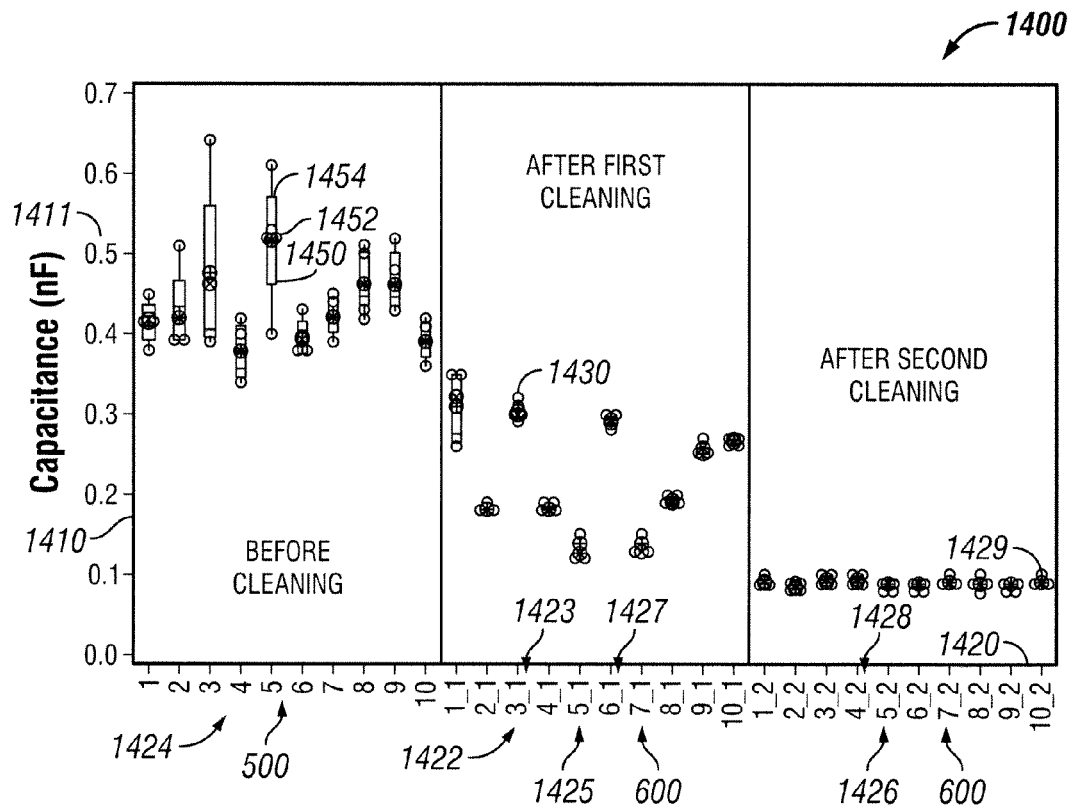
FIG. 14 is a data scattering chart that shows the measured capacitance values for a plurality of intermediately leached and/or intermediately cleaned cutters at different cleaning cycles according to an exemplary embodiment.

FIG. 14 is a data scattering chart 1400 that shows the measured capacitance values 1411 for a plurality of intermediately leached and/or intermediately cleaned cutters 500, 600 at different cleaning cycles according to an exemplary embodiment. Referring to FIG. 14, the data scattering chart 1400 includes a cutter number axis 1420 and a capacitance axis 1410. The cutter number axis 1420 includes the number of the cutters 1422 tested along with a cleaning cycle number 1423. As shown, the first set of cutter numbers 1424 has not been cleaned of by-product materials 398 (FIG. 5), the second set of cutter numbers 1425 has been cleaned of by-product materials 398 (FIG. 5) through a first cleaning cycle 1427, and the third set of cutter numbers 1426 has been cleaned of by-product materials 398 (FIG. 5) through a second cleaning cycle 1428. The capacitance axis 1410 includes values for the measured capacitance 1411. A capacitance data point 1430 is obtained by measuring the capacitance of the intermediately leached and/or intermediately cleaned cutter 500, 600, or intermediately leached and/or intermediately cleaned component, using the capacitance measuring system 1200 (FIG. 12), the capacitance measuring system 1300 (FIG. 13), or a similar type system. Each capacitance data point 1430 for each cutter number 1422, with its respective cleaning cycle number 1423, is plotted on the data scattering chart 1400. Each cutter number 1422 has its capacitance measured a plurality of times. In some exemplary embodiments, five capacitance data points 1430 are obtained for each cutter number 1422, however, the number of measurements is greater or fewer in other exemplary embodiments. In some exemplary embodiments, a twenty-five percentile marking 1450, a fifty percentile marking 1452 (or average), and a seventy-five percentile marking 1454 are shown in the chart 1400 for each cutter number 1422. The area between the twenty-five percentile marking 1450 and the seventy-five percentile marking 1454 is shaded. The amount of data scattering is ascertained using this data scattering chart 1400 and can be one or more of a differential between the highest and lowest capacitance measurements 1411 for each cutter number 1422, a range between the twenty-five percentile marking 1450 and the seventy-five percentile marking 1454, or some similar observation made from the data scattering chart 1400.

According to FIG. 14, the first set of cutter numbers 1424, which has not yet been cleaned, shows a larger data scattering of capacitance values 1411 than when compared to the second set of cutter numbers 1425, which has been cleaned once for one hour using the by-products removal apparatus 700 (FIG. 7), the by-products removal apparatus 800 (FIG. 8), the by-products removal apparatus 900 (FIG. 9), or the by-products removal apparatus 1000 (FIG. 10). Further, the second set of cutter numbers 1425, which has been cleaned once for one hour using the by-products removal apparatus 700 (FIG. 7), the by-products removal apparatus 800 (FIG. 8), the by-products removal apparatus 900 (FIG. 9), or the by-products removal apparatus 1000 (FIG. 10), shows a larger data scattering of capacitance values 1411 than when compared to the third set of cutter numbers 1426, which has been cleaned a second time for another one hour using the by-products removal apparatus 700 (FIG. 7), the by-products removal apparatus 800 (FIG. 8), the by-products removal apparatus 900 (FIG. 9), or the by-products removal apparatus 1000 (FIG. 10). The third set of cutter numbers 1426 exhibit a minimal, or negligible, amount of data scattering of capacitance values 1411. Thus, the capacitance values 1411 of the third set of cutter numbers 1426 is the stable lower limit capacitance value 1429 in this exemplary embodiment. However, it is possible, that if the third set of cutter numbers 1426 was to undergo an additional cleaning cycle, the capacitance values 1411 of the fourth set of cutter numbers (not shown) would be the stable lower limit capacitance value. When the stable lower limit capacitance value 1429 is reached, i.e. there is minimal to no data scattering of capacitance values 1411, the intermediately cleaned leached PDC cutters 600 are effectively cleaned and verified as such.

Referring back to FIG. 11, the by-product materials removal verification method 1100 proceeds to step 1160. At step 1160, the by-product materials removal verification method 1100 ends.

Referring back to FIG. 4, the leaching method 400 proceeds to step 450. At step 450, the leaching process and the cleaning process continue iteratively and alternatingly on the intermediately cleaned leached PDC cutter 600 (FIG. 6) until the depth of the leached portion 554 (FIG. 5) reaches a desired leaching depth 353 (FIG. 3). In some exemplary embodiments, however, the leaching process and the cleaning process are not performed alternatingly, but one or more processes are performed consecutively before the other process is performed. Once the desired leaching depth 353 is reached, a cleaned leached PDC cutter 1500 (FIG. 15) is formed. As previously mentioned, cleaning the intermediately leached PDC cutter 500 (FIG. 5) to form the intermediately cleaned leached PDC cutter 600 (FIG. 6) allows the subsequent leaching process that is performed to be at a faster rate than if the intermediately leached PDC cutter 500 (FIG. 5) was not cleaned. Hence, the cleaned leached PDC cutter 1500 (FIG. 15) is formed in a shorter duration than if it were to be formed using a single leaching process and a single cleaning process on the PDC cutter 100 (FIG. 1).

Figure 15:
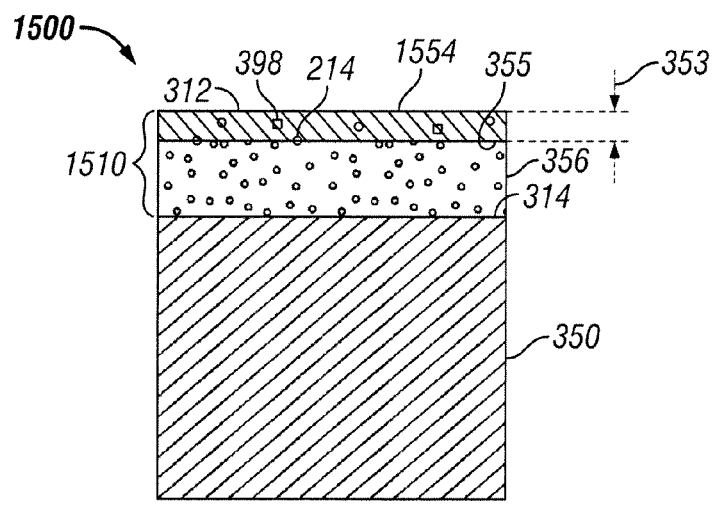
FIG. 15 shows a cross-sectional view of the cleaned leached PDC cutter having a PCD cutting table that has been leached to the desired leaching depth in accordance with an exemplary embodiment.

FIG. 15 shows a cross-sectional view of the cleaned leached PDC cutter 1500 having a PCD cutting table 1510 that has been leached and cleaned to the desired leaching depth 353 in accordance with an exemplary embodiment. The cleaned leached PDC cutter 1500 has been exposed to two or more leaching cycles and at least one cleaning cycle. Referring to FIG. 15, the cleaned leached PDC cutter 1500 includes the PCD cutting table 1510 coupled to the substrate 350. The substrate 350 has been previously described above with respect to FIG. 3 and therefore is not described again for the sake of brevity. The PCD cutting table 1510 is similar to the PCD cutting table 310 (FIG. 3), but has had at least a portion of the by-product materials 398 removed from a cleaned leached layer 1554. The cleaned leached layer 1554 is similar to leached layer 354 (FIG. 3) except that at least a portion of the by-product materials 398 is removed from the leached layer 354 (FIG. 3) to form the cleaned leached layer 1554. Thus, PCD cutting table 1510 includes the cleaned leached layer 1554 and the unleached layer 356 which is disposed between the cleaned leached layer 1554 and the substrate 350. The cleaned leached layer 1554 extends from the cutting surface 312, which has been described above with respect to FIG. 3, towards the opposing surface 314, which also has been described with respect to FIG. 3. In the cleaned leached layer 1554, at least a portion of the cobalt 214 has been removed from within the interstitial spaces 212 (FIG. 2) using at least one leaching process mentioned above when compared to the PCD cutting table 110 (FIG. 1). Thus, the cleaned leached layer 1554 has been leached to the desired leaching depth 353. However, as previously mentioned above, one or more by-product materials 398 were formed and deposited within some of the interstitial spaces 212 (FIG. 2) in the leached layer 354 (FIG. 3) during the leaching process. However, at least a portion of these by-product materials 398 are removed from the leached layer 354 (FIG. 3), thereby forming leached layer 1554. The process of removing the by-product materials 398 from the leached layer 354 (FIG. 3) has been described above and is not repeated again herein. The unleached layer 356 has been previously described with respect to FIG. 3 and therefore is not repeated for the sake of brevity. Although the boundary line 355 is formed between the cleaned leached layer 1554 and the unleached layer 356 and is depicted as being substantially linear, the boundary line 355 can be non-linear.

Referring back to FIG. 4, the leaching method proceeds to step 460. At step 460, the leaching method 400 ends.

A cleaned leached PDC cutter, which is substantially free of by-product materials, or catalyst metal salts, has a superior wear abrasion resistance with an increased thermal stability. Thus, the apparatus and methods disclosed herein minimizes the detrimental effects of the leaching reaction by-product materials. Further, a cleaning cycle occurring intermittently between successive leaching cycles allows the subsequent leaching cycle to proceed at a faster rate. Removing at least a portion of the by-product materials trapped within the leached portion has a beneficial effect of allowing the leaching solution to infiltrate into the polycrystalline structure faster and deeper. Although the conventional leaching method allows the leaching depth to reach about 300 microns only after long treatment periods, which are at times in excess of several days, the leaching method 400 allows the leaching depths to be reached in much shorter time periods or to reach the entire thickness of the polycrystalline structure in a few day. Conventional leaching process typically takes several weeks of treatment time when leaching the entire depth of the polycrystalline structure.

Although each exemplary embodiment has been described in detail, it is to be construed that any features and modifications that are applicable to one embodiment are also applicable to the other embodiments. Furthermore, although the invention has been described with reference to specific embodiments, these descriptions are not meant to be construed in a limiting sense. Various modifications of the disclosed embodiments, as well as alternative embodiments of the invention will become apparent to persons of ordinary skill in the art upon reference to the description of the exemplary embodiments. It should be appreciated by those of ordinary skill in the art that the conception and the specific embodiments disclosed may be readily utilized as a basis for modifying or designing other structures or methods for carrying out the same purposes of the invention. It should also be realized by those of ordinary skill in the art that such equivalent constructions do not depart from the spirit and scope of the invention as set forth in the appended claims. It is therefore, contemplated that the claims will cover any such modifications or embodiments that fall within the scope of the invention.

What is claimed is:

1. A leaching method for removing at least a portion of a catalyst material from within a polycrystalline structure, the catalyst material being removed from one end of the polycrystalline structure to a desired leaching depth of the polycrystalline structure, the method comprising:
    obtaining a cutter comprising a substrate and a polycrystalline structure, the polycrystalline structure comprising a first end and a second end opposite the first end, wherein the second end of the polycrystalline structure is coupled to the substrate;
    performing a leaching process on the polycrystalline structure until at least a portion of the catalyst material is removed from an intermediate leaching depth of the polycrystalline structure, the leaching process forming at least some by-product materials deposited within the intermediate leaching depth of the polycrystalline structure;
    performing a cleaning process on the polycrystalline structure until at least a portion of the by-product materials is removed from the intermediate leaching depth of the polycrystalline structure;
    determining an effectiveness of the cleaning process using a capacitance measuring system comprising;
        a capacitance measuring device comprising a first terminal and a second terminal;
        the cutter;
        a first wire electrically coupled to the first end of the polycrystalline structure and the first terminal; and
        a second wire electrically coupled to an end of the substrate and the second terminal; and
    continuing iteratively performing the leaching process and performing the cleaning process on the polycrystalline structure until the intermediate leaching depth reaches a desired leaching depth,
    wherein a different intermediate leaching depth is reached during each leaching process and each different intermediate leaching depth progresses towards the desired leaching depth, and
    wherein the desired leaching depth is greater than at least one intermediate leaching depth.

2. The leaching method of claim 1, wherein continuing iteratively performing the leaching process and performing the cleaning process on the polycrystalline structure comprises:
    performing the leaching process and performing the cleaning process on the polycrystalline structure in an alternating manner.

3. The leaching method of claim 1, wherein continuing iteratively performing the leaching process and performing the cleaning process on the polycrystalline structure comprises:
    performing a plurality of cleaning processes on the polycrystalline structure until a measured capacitance of the polycrystalline structure is at a stable lower limit capacitance value before performing the leaching process on the polycrystalline structure.

4. The leaching method of claim 1, wherein the leaching process comprises immersing at least a portion of the polycrystalline structure into an acidic solution.

5. The leaching method of claim 1, wherein the cleaning process comprises immersing at least a portion of the polycrystalline structure into a cleaning fluid.

6. The leaching method of claim 5, wherein the cleaning fluid comprises de-ionized water.

7. The leaching method of claim 1, wherein the cleaning process comprises providing a transducer to emit acoustic waves into the polycrystalline structure.

8. A leaching method for removing at least a portion of a catalyst material from within a polycrystalline structure, the catalyst material being removed from one end of the polycrystalline structure to a desired leaching depth of the polycrystalline structure, the method comprising:
    obtaining a component comprising a polycrystalline structure, the polycrystalline structure comprising a first end and a second end opposite the first end;
    performing a leaching process on the polycrystalline structure until at least a portion of the catalyst material is removed from an intermediate leaching depth of the polycrystalline structure, the leaching process forming at least some by-product materials deposited within the intermediate leaching depth of the polycrystalline structure, the intermediate leaching depth being measured from the first end;
    performing a cleaning process on the polycrystalline structure until at least a portion of the by-product materials is removed from the intermediate leaching depth of the polycrystalline structure;
    determining an effectiveness of the cleaning process using a capacitance measuring system comprising;
    a capacitance measuring device comprising a first terminal and a second terminal;
    the component comprising the polycrystalline structure;
    a first wire electrically coupled to the first end of the polycrystalline structure and the first terminal; and
    a second wire electrically coupled to the component and the second terminal; and continuing iteratively performing the leaching process and performing the cleaning process on the polycrystalline structure until the intermediate leaching depth reaches a desired leaching depth, the desired leaching depth being measured from the first end, wherein a different intermediate leaching depth is reached during each leaching process and each different intermediate leaching depth progresses towards the desired leaching depth, wherein the desired leaching depth is greater than at least one intermediate leaching depth, and wherein one or more cleaning processes is performed for a desired cleaning period.

9. The leaching method of claim 8, wherein the component is a cutter comprising a substrate and the polycrystalline structure, wherein the second end of the polycrystalline structure is coupled to the substrate.

10. The leaching method of claim 9, wherein the second wire of the capacitance measuring system is electrically coupled to an end of the substrate and the second terminal.

11. The leaching method of claim 8, wherein continuing iteratively performing the leaching process and performing the cleaning process on the polycrystalline structure comprises:

performing the leaching process and performing the cleaning process on the polycrystalline structure in an alternating manner.

12. The leaching method of claim 8, wherein continuing iteratively performing the leaching process and performing the cleaning process on the polycrystalline structure comprises:

performing a plurality of cleaning processes on the polycrystalline structure until a measured capacitance of the polycrystalline structure is at a stable lower limit capacitance value before performing the leaching process on the polycrystalline structure.

13. The leaching method of claim 8, wherein the leaching process comprises immersing at least a portion of the polycrystalline structure into an acidic solution.

14. The leaching method of claim 8, wherein the cleaning process comprises immersing at least a portion of the polycrystalline structure into a cleaning fluid.

15. The leaching method of claim 14, wherein the cleaning fluid comprises de-ionized water.

16. The leaching method of claim 8, wherein the cleaning process comprises providing a transducer to emit acoustic waves into the polycrystalline structure.

17. The leaching method of claim 8, wherein continuing iteratively performing the leaching process and performing the cleaning process on the polycrystalline structure comprises:

performing a plurality of cleaning processes on the polycrystalline structure for one or more desired cleaning periods before performing the leaching process on the polycrystalline structure.

18. The leaching method of claim 8, wherein an effectiveness of the cleaning process is determined by the amount of time the polycrystalline structure is cleaned.

* * * * *